United States Patent [19]

Yamada et al.

[11] Patent Number: 5,376,639

[45] Date of Patent: Dec. 27, 1994

[54] TREATMENT OF SARCOMA WITH INTERLEUKIN 1α POLYPEPTIDES

[75] Inventors: Masaaki Yamada, Kyoto; Yasuji Furutani; Michiko Yamayoshi, both of Toyonaka; Mitsue Notake, Suita; Junichi Yamagishi, Nara, all of Japan

[73] Assignee: Dainippon Pharmaceutical Co., Ltd., Osaka, Japan

[21] Appl. No.: 954,418

[22] Filed: Sep. 30, 1992

Related U.S. Application Data

[60] Continuation of Ser. No. 496,800, Mar. 21, 1990, abandoned, which is a division of Ser. No. 812,796, Dec. 23, 1985, abandoned.

[30] Foreign Application Priority Data

| Dec. 25, 1984 | [JP] | Japan | 59-278665 |
| Feb. 28, 1985 | [JP] | Japan | 60-39762 |
| May 24, 1985 | [JP] | Japan | 60-112474 |
| Aug. 2, 1985 | [JP] | Japan | 60-171493 |
| Sep. 11, 1985 | [JP] | Japan | 60-200894 |

[51] Int. Cl.$^5$ .............................. A61K 37/02
[52] U.S. Cl. ........................ 514/12; 424/85.2; 530/351; 930/141
[58] Field of Search ............ 424/85.1; 512/2, 8, 512/12

[56] References Cited

U.S. PATENT DOCUMENTS

| 4,816,436 | 3/1989 | Jacobs | 514/2 |
| 5,039,790 | 8/1991 | Adams et al. | 530/351 |
| 5,047,505 | 9/1991 | Huang | 530/351 |
| 5,075,288 | 12/1991 | Krueger et al. | 530/351 |

FOREIGN PATENT DOCUMENTS

| A-0161901 | 11/1985 | European Pat. Off. |
| A-0161935 | 11/1985 | European Pat. Off. |
| A-0165654 | 12/1985 | European Pat. Off. |
| A-0188864 | 7/1986 | European Pat. Off. |
| 0324447 | 7/1989 | European Pat. Off. |

OTHER PUBLICATIONS

Auron, et al. (1984) *Lymphokine Research* 3, 285.
Auron, et al. (1984) *Proc. Natl. Acad. Sci. USA* 81, 7907.
Furutani et al. (1985) *Nucleic Acids Res.* 13, 5869.
Krakauer (1985) *Preparative Biochemistry* 14, 449.
Kronheim, et al. (1985) *Journal of Experimental Medicine* 161, 490.
Lomedico, et al. (1984) *Nature* 312, 458.
March, et al. (1985) *Nature* 315, 641.
Mosley, et al. (1985) *Progress in Leukocyte Biology* 2, 521.
Scala, et al. (1984) *Nature* 309, 56.
Durum et al., *Ann. Rev. Immunol* 1985, 3, pp. 263–287.
Immunophysical: The Rate of Cells and Cytakines in Immunity and Inflammation, Opperheim et al., 1990, pp. 210–214.

*Primary Examiner*—Garnette D. Draper
*Assistant Examiner*—L. Spector
*Attorney, Agent, or Firm*—Scully, Scott, Murphy & Presser

[57] ABSTRACT

DNAs encoding polypeptides having interleukin 1, vectors inserted with said DNAs, hosts transformed with said recombinant vectors, polypeptides having interleukin 1 activity which are produced by cultivation of the transformed hosts, derivatives of the polypeptides, pharmaceutical composition containing said polypeptides or derivatives, their use as an antitumor or antiinfectious agent, and processes for the preparation thereof.

1 Claim, 11 Drawing Sheets

```
  1                              30                                      60
ATG GCC AAA GTT CCA GAC ATG TTT GAA GAC CTG AAG AAC TGT TAC AGT GAA AAT GAA GAA
Met Ala Lys Val Pro Asp Met Phe Glu Asp Leu Lys Asn Cys Tyr Ser Glu Asn Glu Glu
                                 10                                      20

90                                     120
GAC AGT TCC TCC ATT GAT CAT CTG TCT CTG AAT CAG AAA TCC TTC TAT CAT GTA AGC TAT
Asp Ser Ser Ser Ile Asp His Leu Ser Leu Asn Gln Lys Ser Phe Tyr His Val Ser Tyr
                                 30                                      40

150                                     180
GGC CCA CTC CAT GAA GGC TGC ATG GAT CAA TCT GTG TCT CTG AGT ATC TCT GAA ACC TCT
Gly Pro Leu His Glu Gly Cys Met Asp Gln Ser Val Ser Leu Ser Ile Ser Glu Thr Ser
                                 50                                      60

210                                     240
AAA ACA TCC AAG CTT ACC TTC AAG GAG AGC ATG GTG GTA GTA GCA ACC AAC GGG AAG GTT
Lys Thr Ser Lys Leu Thr Phe Lys Glu Ser Met Val Val Val Ala Thr Asn Gly Lys Val
                                 70                                      80

270                                     300
CTG AAG AAG AGA CGG TTG AGT TTA AGC CAA TCC ATC ACT GAT GAT GAC CTG GAG GCC ATC
Leu Lys Lys Arg Arg Leu Ser Leu Ser Gln Ser Ile Thr Asp Asp Asp Leu Glu Ala Ile
                                 90                                     100

330                                     360
GCC AAT GAC TCA GAG GAA GAA ATC ATC AAG CCT AGG TCA TCA CCT TTT AGC TTC CTG AGC
Ala Asn Asp Ser Glu Glu Glu Ile Ile Lys Pro Arg Ser Ser Pro Phe Ser Phe Leu Ser
                                110                                     120

390                                     420
AAT GTG AAA TAC AAC TTT ATG AGG ATC ATC AAA TAC GAA TTC ATC CTG AAT GAC GCC CTC
Asn Val Lys Tyr Asn Phe Met Arg Ile Ile Lys Tyr Glu Phe Ile Leu Asn Asp Ala Leu
                                130                                     140

450                                     480
AAT CAA AGT ATA ATT CGA GCC AAT GAT CAG TAC CTC ACG GCT GCT GCA TTA CAT AAT CTG
Asn Gln Ser Ile Ile Arg Ala Asn Asp Gln Tyr Leu Thr Ala Ala Ala Leu His Asn Leu
                                150                                     160

510                                     540
GAT GAA GCA GTG AAA TTT GAC ATG GGT GCT TAT AAG TCA TCA AAG GAT GAT GCT AAA ATT
Asp Glu Ala Val Lys Phe Asp Met Gly Ala Tyr Lys Ser Ser Lys Asp Asp Ala Lys Ile
                                170                                     180

570                                     600
ACC GTG ATT CTA AGA ATC TCA AAA ACT CAA TTG TAT GTG ACT GCC CAA GAT GAA GAC CAA
Thr Val Ile Leu Arg Ile Ser Lys Thr Gln Leu Tyr Val Thr Ala Gln Asp Glu Asp Gln
                                190                                     200

630                                     660
CCA GTG CTG CTG AAG GAG ATG CCT GAG ATA CCC AAA ACC ATC ACA GGT AGT GAG ACC AAC
Pro Val Leu Leu Lys Glu Met Pro Glu Ile Pro Lys Thr Ile Thr Gly Ser Glu Thr Asn
                                210                                     220

690                                     720
CTC CTC TTC TTC TGG GAA ACT CAC GGC ACT AAG AAC TAT TTC ACA TCA GTT GCC CAT CCA
Leu Leu Phe Phe Trp Glu Thr His Gly Thr Lys Asn Tyr Phe Thr Ser Val Ala His Pro
                                230                                     240

750                                     780
AAC TTG TTT ATT GCC ACA AAG CAA GAC TAC TGG GTG TGC TTG GCA GGG GGG CCA CCC TCT
Asn Leu Phe Ile Ala Thr Lys Gln Asp Tyr Trp Val Cys Leu Ala Gly Gly Pro Pro Ser
                                250                                     260

810                                     840
ATC ACT GAC TTT CAG ATA CTG GAA AAC CAG GCG TAG GTC TGG AGT CTC ACT TGT CTC ACT
Ile Thr Asp Phe Gln Ile Leu Glu Asn Gln Ala ***
                                270

(Note): 1) *** means the stop codon.
               2) The bracket means the region coding for mature IL-1.

FIG.11
```

```
  1                                   30                                    60
ATG GCC AAA GTC CCT GAT CTG TTT GAA GAC CTA AAG AAC TGT TTC AGT GAA AAT GAG GAA
Met Ala Lys Val Pro Asp Leu Phe Glu Asp Leu Lys Asn Cys Phe Ser Glu Asn Glu Glu
                                     10                                    20

90                                   120
TAC AGC TCT GCC ATT GAC CAT CTT TCT CTG AAT CAG AAA TCC TTC TAT GAT GCA AGC TAT
Tyr Ser Ser Ala Ile Asp His Leu Ser Leu Asn Gln Lys Ser Phe Tyr Asp Ala Ser Tyr
                                     30                                    40

150                                   180
GAA CCA CTT CAT GAA GAC TGC ATG AAT AAA GTT GTG TCT CTG AGT ACC TCT GAA ACC TCT
Glu Pro Leu His Glu Asp Cys Met Asn Lys Val Val Ser Leu Ser Thr Ser Glu Thr Ser
                                     50                                    60

210                                   240
GTG TCA CCC AAC CTC ACC TTC CAG GAG AAT GTG GTG GCA GTA ACA GCC AGT GGG AAG ATT
Val Ser Pro Asn Leu Thr Phe Gln Glu Asn Val Val Ala Val Thr Ala Ser Gly Lys Ile
                                     70                                    80

270                                   300
CTG AAG AAA AGA CGC TTG AGT TTA AAC CAG CCC ATC ACT GAT GTT GAC CTG GAG ACC AAT
Leu Lys Lys Arg Arg Leu Ser Leu Asn Gln Pro Ile Thr Asp Val Asp Leu Glu Thr Asn
                                     90                                   100

330                                   360
GTC AGT GAT CCA GAA GAA GGA ATC ATC AAG CCC AGA TCA GTT CCT TAC ACC TTC CAG AGA
Val Ser Asp Pro Glu Glu Gly Ile Ile Lys Pro Arg Ser Val Pro Tyr Thr Phe Gln Arg
                                    110                                   120

390                                   420
AAT ATG AGA TAC AAA TAC TTG AGA ATC ATC AAA CAA GAG TTT ACC CTG AAT GAT GCT CTC
Asn Met Arg Tyr Lys Tyr Leu Arg Ile Ile Lys Gln Glu Phe Thr Leu Asn Asp Ala Leu
                                    130                                   140

450                                   480
AAT CAA AGC CTA GTT CGT GAC ACC TCA GAT CAG TAC CTC AGG GCA GCT CCA CTA CAA AAT
Asn Gln Ser Leu Val Arg Asp Thr Ser Asp Gln Tyr Leu Arg Ala Ala Pro Leu Gln Asn
                                    150                                   160

510                                   540
CTG GGC GAT GCA GTG AAA TTT GAC ATG GGG GTC TAC ATG ACA TCA GAG GAT TCT ATA CTT
Leu Gly Asp Ala Val Lys Phe Asp Met Gly Val Tyr Met Thr Ser Glu Asp Ser Ile Leu
                                    170                                   180

570                                   600
CCT GTA ACT TTA AGA ATC TCA CAA ACT CCA CTG TTT GTG AGT GCC CAG AAT GAA GAT GAA
Pro Val Thr Leu Arg Ile Ser Gln Thr Pro Leu Phe Val Ser Ala Gln Asn Glu Asp Glu
                                    190                                   200

630                                   660
CCT GTG CTG CTA AAG GAA ATG CCT GAG ACA CCC AGG ATC ATC ACA GAC AGC GAG AGT GAC
Pro Val Leu Leu Lys Glu Met Pro Glu Thr Pro Arg Ile Ile Thr Asp Ser Glu Ser Asp
                                    210                                   220

690                                   720
ATC CTC TTC TTC TGG GAA ACT CAA GGC AAT AAG AAC TAC TTC AAG TCA GCA GCC AAC CCA
Ile Leu Phe Phe Trp Glu Thr Gln Gly Asn Lys Asn Tyr Phe Lys Ser Ala Ala Asn Pro
                                    230                                   240

750                                   780
CAG CTG TTT ATT GCC ACA AAG CCA GAA CAT CTG GTG CAC ATG GCA AGG GGG TTA CCT TCG
Gln Leu Phe Ile Ala Thr Lys Pro Glu His Leu Val His Met Ala Arg Gly Leu Pro Ser
                                    250                                   260

801
ATG ACT GAT TTT CAG ATC TCA TAA
Met Thr Asp Phe Gln Ile Ser ***
                         267
```

(Note): 1) *** means the stop codon.
2) The bracket means the region coding for mature IL-1.

FIG.12

TREATMENT OF SARCOMA WITH INTERLEUKIN 1α POLYPEPTIDES

This is a continuation of copending application(s) Ser. No. 496,800 filed on Mar. 21, 1990, now abandoned. Which is a divisional of Ser. No. 812,796 filed Dec. 23, 1985 abandoned.

This invention relates to a DNA encoding a polypeptide having interleukin 1 activity, a vector having said DNA inserted thereinto, a host transformed with said vector, a polypeptide having interleukin 1 activity which is produced by cultivation of the transformed host, derivatives of the polypeptide, a pharmaceutical composition containing said polypeptide or derivative, their use as an antitumor or antiinfectious agent, and processes for the preparation thereof.

PRIOR ART

Gery et al., demonstrated the presence of a substance which augments the mouse thymocyte proliferation by mitogen in the culture medium of macrophage, which has been called "lymphocytes activating factor" (LAF). Since 1979, it has been designated as "interleukin 1" (abbreviated as "IL-1"), and hence, in this specification, it is called as interleukin 1.

It is known that IL-1 promotes proliferation of T and B lymphocytes and further acts on T lymphocyte and thereby promotes the production of lymphokines, particularly interleukin 2 (T lymphocyte proliferation factor), and hence it is one of the important factors which take a role on the production of antibody and the control of cellular immunity [cf. Staruch, M. J., et al., J. Immunol., 130, 2191 (1983)]. It is also reported that IL-1 is effective on the production of prostaglandin E or collagenase, proliferation of fibroblast, and enhancement of natural killer (NK) cell activation by interleukin 2 or interferon [Simon, P. L., et al., "Lymphokines" Vol. 6, 47 (1982), Academic Press Inc.].

Thus, IL-1 participates not only immune response but also protective and repairing mechanisms in vivo, and hence is expected to be used as a medicament.

IL-1 has been produced by culturing macrophage, peripheral mononuclear cells, macrophage-like cells (e.g. mouse P388D$_1$ cells), or monocytic or myelocytic leukemia cells in the presence of an appropriate inducer and then isolating from the culture medium, but the structure of the IL-1 has not been clear.

It has been reported that human IL-1 isolated from the culture medium of human monocytic leukemia cells (e.g. U937 cells) or human peripheral mononuclear cells has a molecular weight of 11,300 and 15,000 daltons [Mizel, S. B., et al., J. Immunol., 131, 1834 (1983); Schmidt, J. A., J. Exp. Med., 160, 772 (1984)].

It has recently been reported that cDNA encoding mouse IL-1 polypeptide has been cloned from mouse P388D$_1$ cells and mouse IL-1 polypeptide consisting of 156 amino acids has been produced in *Escherichia coli* [Lomedico, P. T., et al., Nature, 312, 458 (1984)]. It has also been reported that cDNA encoding human IL-1 polypeptide has been cloned from human mononuclear cells and the expression thereof has been succeeded [Auron, P. E., et al., Proc. Natl. Acad. Sci. USA, 81, 7907 (1984)].

However, the polypeptides and DNAs encoding them of this invention are clearly different from the above known products to distinguish IL-1 of the present invention from those known in the prior art, the instant IL-1 shall be designated IL-1a. Hereinafter, all occurrences of IL-1 herein shall pertain to IL-1a.

There is no report as to rabbit IL-1 polypeptide and DNA encoding it.

BRIEF SUMMARY OF THE INVENTION

The present inventors have intensively studied on the production of IL-1 by genetic engineering technique and have suceeded in cloning DNAs encoding human IL-1 and rabbit IL-1 and in the transformation of a host with an expression vector containing the cloned DNA and have confirmed that the transformed host can produce IL-1 or a substance having IL-1 activity.

That is, the present inventors have succeeded in the production of a polypeptide having human or rabbit IL-1 activity by cultivating human cells which have been differentiated into macrophage-like cells or rabbit macrophages in the presence of an inducer(s) suitable for producing IL-1 and thereby accumulating IL-1 mRNA in the cells, preparing a cDNA library by using the mRNA as a template, cloning a DNA encoding human or rabbit IL-1 therefrom, determining whole nucleotide sequence of said DNA, and inserting the cloned DNA into an expression vector, and then transforming a host with the vector to give a transformed host which can produce the desired polypeptide having IL-1 activity. In the course of the study, the present inventors have found that the human or rabbit IL-1 is formed as a precursor and that the polypeptide consisting of 159 amino acids at the C-terminus of said human IL-1 precursor has potent IL-1 activity with molecular weight of 18,000 and pI 5.3. Based on such findings, the present inventors have specified that this polypeptide is mature human IL-1 and further that mature rabbit IL-1 is a polypeptide consisting of 155 amino acids at the C-terminus of the rabbit IL-1 precursor by judging from the homology.

In this invention, the polypeptide consisting of 159 amino acids at the C-terminus of said human IL-1 precursor and the polypeptide consisting of 155 amino acids at the C-terminus of said rabbit IL-1 procursor are referred to as a mature human IL-1 and a mature rabbit IL-1, respectively.

Moreover, it has been found that mature polypeptides having less amino acid sequences than the sequences of the mature human IL-1 polypeptide consisting of 159 amino acid residues show also IL-1 activity like mature human IL-1 polypeptide. Besides, high homologies have been found between the nucleotide sequences coding for human and rabbit IL-1 polypeptides, and between the deduced amino acid sequences of human and rabbit IL-1 polypeptides. It may be suggested therefrom that human and rabbit IL-1 polypeptides are phylogenetically derived from the same gene, and that a considerable portion(s) of the common regions are a sequence(s) necessary for their biological activities.

An object of the invention is to provide a DNA encoding a polypeptide having IL-1 activity. Another object of the invention is to provide a vector inserted with the DNA as mentioned above. Another object of the invention is to provide a host transformed with said recombinant vector. A further object of the invention is to provide a polypeptide having IL-1 activity which is produced by cultivation of the transformed host as set forth above. A still further object of the invention is to provide a derivative (substance) obtained from the polypeptide. A still further object of the invention is to provide a pharmaceutical composition containing said polypeptide or derivative as an active ingredient. A more further object of the invention is to provide a process for preparing the DNA, vector, transformed host and polypeptide or derivative. These and other objects and advantages of the invention will be apparent to person skilled in the art from the following description.

BRIEF DESCRIPTION OF DRAWINGS

FIG. 11 shows the nucleotide sequence and the corresponding amino acid sequence from the coding region of the human IL-1 gene and is the same as Table 5.

FIG. 12 shows the nucleotide sequence and the corresponding amino acid sequence from the coding region of the rabbit IL-1 gene and is the same as Table 7.

DETAILED DESCRIPTION OF THE INVENTION

Figure 1B:
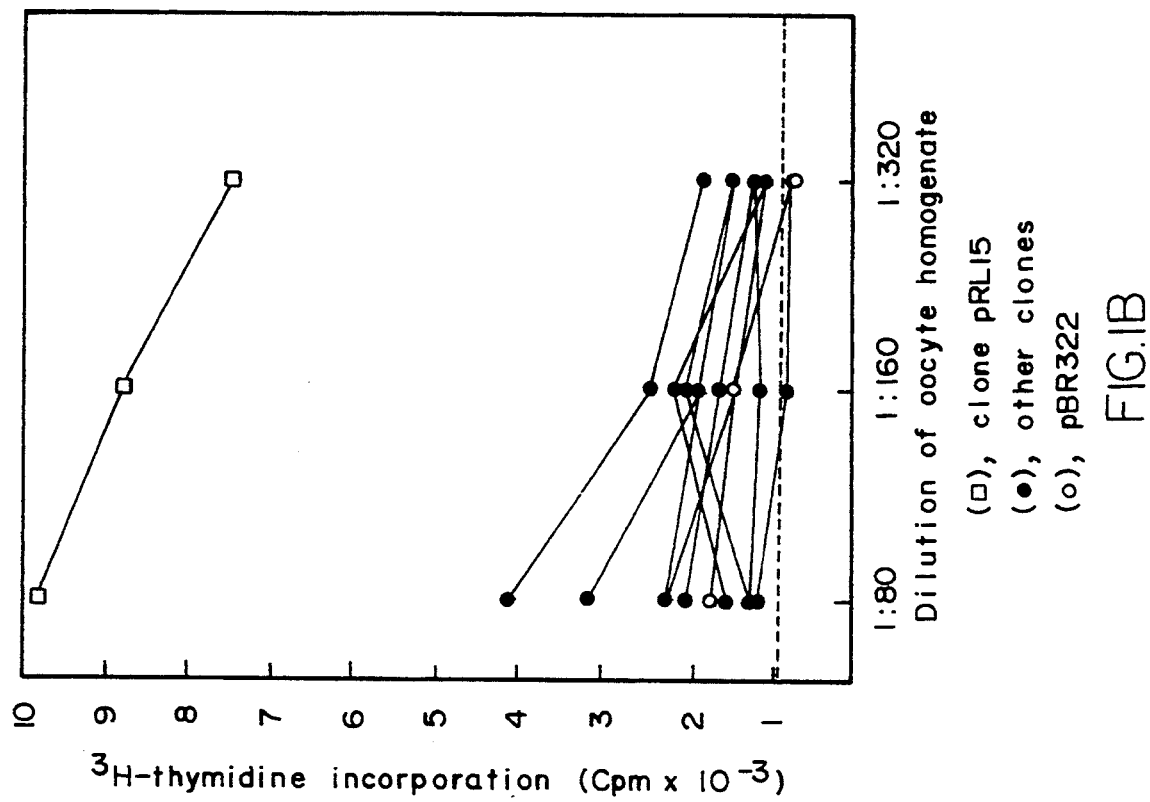
FIGS. 1A and B show the test result of hybridization translation in cloning of cDNA of rabbit IL-1, wherein the dotted line means $^3$H-thymidine incorporation in the control.
Figure 1A:
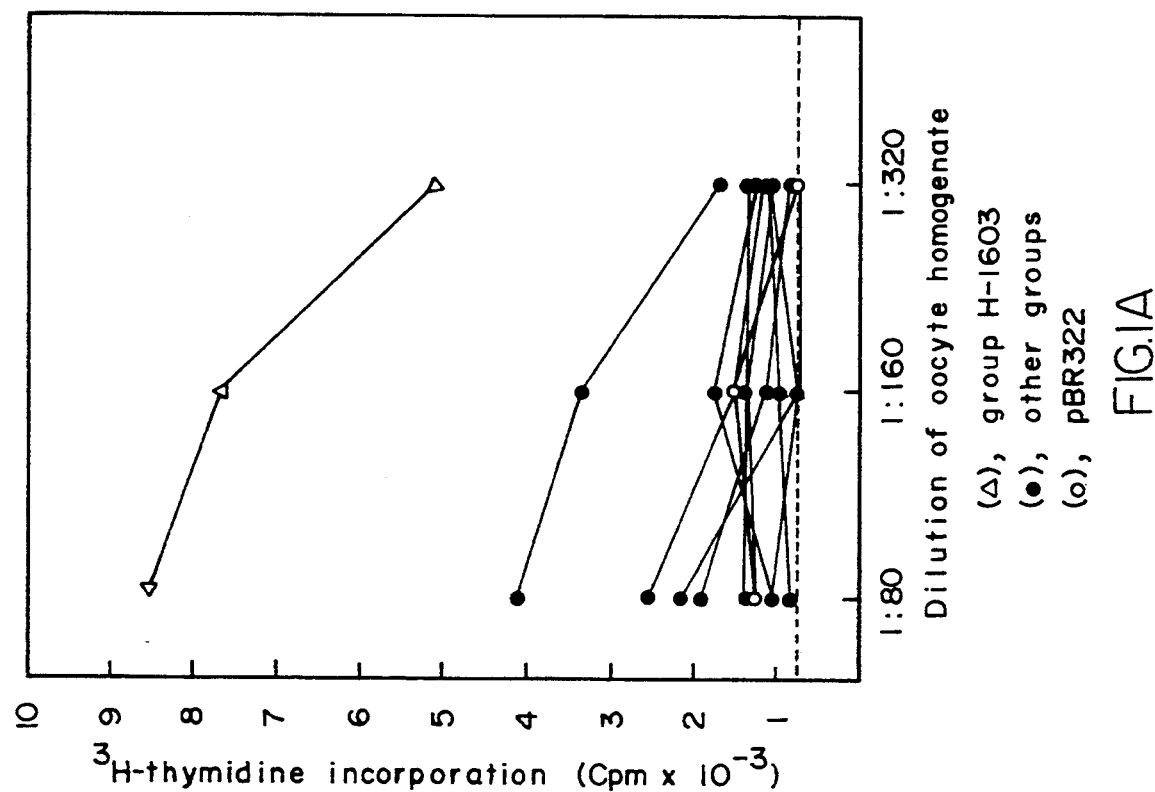

For simplification of the description, the following abbreviations are used in the present specification and claims.

| | |
|---|---|
| A: | adenine |
| C: | cytosine |
| G: | guanine |
| T: | thymine |
| Ala: | alanine |
| Arg: | arginine |
| Asn: | asparagine |
| Asp: | aspartic acid |
| Cys: | cysteine |
| Gln: | glutamine |
| Glu: | glutamic acid |
| Gly: | glycine |
| His: | histidine |
| Ile: | isoleucine |
| Leu: | leucine |
| Lys: | lysine |
| Met: | methionine |
| Phe: | phenylalanine |
| Pro: | proline |
| Ser: | serine |
| Thr: | threonine |
| Trp: | tryptophan |
| Tyr: | tyrosine |
| Val: | valine |
| DNA: | deoxyribonucleic acid |
| cDNA: | complementary DNA |
| sscDNA: | single-stranded cDNA |
| dscDNA: | double-stranded cDNA |
| RNA: | ribonucleic acid |
| mRNA: | messenger RNA |
| poly(A)mRNA: | poly(A)-containing mRNA |
| dATP: | deoxyadenosine triphosphate |
| dCTP: | deoxycytidine triphosphate |
| dGTP: | deoxyguanosine triphosphate |
| dTTP: | deoxythymidine triphosphate |
| oligo(dC): | oligodeoxycytidylic acid |
| oligo(dG): | oligodeoxguanylic acid |
| oligo(dT): | oligodeoxythymidylic acid |
| poly(A): | polyadenylic acid |
| poly(U): | polyuridylic acid |
| poly(dC): | polydeoxycytidylic acid |
| poly(dG): | polydeoxyguanylic acid |
| ATP: | adenosine triphosphate |
| EDTA: | ethylenediaminetetraacetic acid |
| kb: | kilobases |
| kbp: | kilobase pairs |
| bp: | base pairs |

In the present specification and claims, the nucleotide sequence shown by a single strand is the nucleotide sequence of a sense strand, and the left end is a 5'-terminus and the right end is a 3'-terminus. In the amino acid sequence, the left end is an N-terminus, and the right end is a C-terminus.

[I] DNAs (A) Designation of DNAs

The DNAs of this invention are DNAs having or containing a nucleotide sequence corresponding to an amino acid sequence represented by the formula [I-1] shown in the attached Table 1-1, wherein one to sixteen, preferably one to fifteen, amino acid residues at the N-terminus and/or one to seven, preferably one to five, amino acid residues at the C-terminus may be deleted, and DNAs having or containing a nucleotide sequence corresponding to an amino acid sequence represented by said formula [I-1] which has, at the N-terminus thereof, further an amino acid sequence represented by the formula [I-2] shown in the attached Table 2-1, wherein an amino acid residue(s) at the N-terminus of the amino acid sequence of the formula [I-2] may be deleted.

These DNAs are ones derived from human gene or cDNA coding for human IL-1.

A DNA consisting of a nucleotide sequence corresponding to an amino acid sequence represented by the formula [I-1] codes for mature human IL-1, and a DNA consisting of the above nucleotide sequence combined at the 5'- terminus thereof with a nucleotide sequence corresponding to an amino acid sequence represented by the formula [I-2] codes for human IL-1 precursor.

The DNAs of this invention includes also DNAs having or containing a nucleotide sequence corresponding to an amino acid sequence represented by the formula [A-1] shown in the attached Table 3-1, which may further have at the N-terminus thereof an amino acid sequence represented by the formula [A-2] shown in the attached Table 4-1, wherein an amino acid residue(s) at the N-terminus of said amino acid sequence of the formula [A-2] may be deleted.

These DNAs are ones derived from rabbit gene or cDNA coding for rabbit IL-1. A DNA consisting of a nucleotide sequence corresponding to an amino acid sequence represented by the formula [A-1] codes for mature rabbit IL-1, and a DNA consisting of the above nucleotide sequence combined at the 5'-terminus thereof with a nucleotide sequence corresponding to an amino acid sequence represented by the formula [A-2] codes for rabbit IL-1 precursor.

Preferred DNAs of this invention are (i) a DNA having a nucleotide sequence corresponding to an amino acid sequence represented by the formula [I-1], (ii) a DNA having a nucleotide sequence corresponding to an amino acid sequence represented by the formula [I-1] in which two amino acid residues at the N-terminus are deleted, (iii) a DNA having a nucleotide sequence corresponding to an amino acid sequence represented by the formula [I-1] in which ten amino acid residues at the N-terminus are deleted, (iv) a DNA having a nucleotide sequence corresponding to an amino acid sequence represented by the formula [I-1] in which fourteen or fifteen amino acid residues at the N-terminus are deleted, (v) a DNA having a nucleotide sequence corresponding to an amino acid sequence represented by the formula [I-1] in which four amino acid residues at the C-terminus are deleted, (vi) a DNA having a nucleotide sequence corresponding to an amino acid sequence represented by the formula [I-1] in which five amino acid residues at the C-terminus are deleted, and (vii) a DNA having a nucleotide sequence corresponding to an amino acid sequence represented by the formula [I-1] in which fifteen amino acid residues at the N-terminus and four amino acid residues at the C-terminus are deleted.

Further, a DNA having a nucleotide sequence corresponding to an amino acid sequence represented by the formula [A-1] is also included as a preferred DNA of this invention.

Above DNAs may have an initiation codon at 5'-terminus and/or a termination codon(s) at the 3'-terminus.

The typical nucleotide sequences corresponding to amino acid sequences represented by the formulae [I-1] and [A-1] are nucleotide sequences represented by the formulae [II-1] and [B-1] shown in Table 1-2 and 3-2, respectively.

The typical nucleotide sequences corresponding to amino acid sequences represented by the formulae [I-2] and [A-2] are nucleotide sequences represented by the formulae [II-2] and [B-2] shown in Tables 2-2 and 4-2, respectively.

It should be understood that the DNAs of this invention include the following DNAs:

a DNA encoding a polypeptide possessing IL-1 activity, a DNA encoding a polypeptide possessing IL-1 activity which is derived from human or rabbit IL-1 gene or cDNA, a cDNA encoding mature human or rabbit IL-1 polypeptide or its precursor, a DNA encoding mature human or rabbit IL-1 polypeptide which is prepared from human or rabbit genomic library, a DNA resulting from chemical or enzymatical modification of a DNA encoding mature human IL-1 polypeptide, a partially or fully synthesized DNA which is substantially the same as the DNA encoding mature human or rabbit IL-1 polypeptide, a DNA with degenerative codons encoding mature human IL-1 polypeptide, its modified polypeptide or rabbit IL-1 polypeptide, a DNA encoding mature human IL-1 polypeptide, its modified polypeptide or rabbit IL-1 polypeptide and having an initiation codon and/or a termination codon(s) and/or a promoter followed by Shine-Dalgarno sequence upstream of the initiation codon, a DNA containing at least a nucleotide sequence(s) which has a highly homologous portion(s) between the nucleotide sequence encoding human IL-1 polypeptide and the nucleotide sequence encoding rabbit IL-1 polypeptide, and a DNA resulting from deletion of a part of 5'-terminal region from a nucleotide sequence encoding human or rabbit IL-1 precursor polypeptide.

(B) Production of DNAs

Processes for the production of the DNAs of the invention will be described hereinbelow.

According to this invention, the DNAs encoding human IL-1 polypeptide and rabbit IL-1 polypeptide can be produced by cultivating human and rabbit macrophages (or macrophage-like cells) together with an inducer(s), separating a fraction containing IL-1 mRNA from the induced cells, preparing a cDNA library from the fraction, and cloning the IL-1 cDNA from the cDNA library.

That is, it can be produced through the following steps:

a) cultivating macrophage or macrophge-like cells together with an inducer(s), b) separating a fraction containing IL-1 mRNA from the induced cells, c) preparing a single-stranded cDNA (sscDNA) from the mRNA by using a reverse transcriptase and then converting it to a double-stranded cDNA (dscDNA), d) inserting the dscDNA into a vector, e) introducing the recombinant vector into a host to transform it and construct a cDNA (colony) library, f) cloning a cDNA encoding IL-1 polypeptide from the library which is constructed by the steps a) to e).

If desired, modification (as step g) of the DNA produced as above can give other DNAs of this invention.

On the other hand, a DNA encoding human or rabbit IL-1 polypeptide can also be obtained by cloning a DNA coding for human or rabbit IL-1 polypeptide from the genomic library (e.g. DNA fragments inserted into bacteriophage Charon 4A), followed by removing intron regions.

The processes for producing the cDNA of this invention will be described in more detail as to the DNA encoding human IL-1 polypeptide or its modified polypeptide. The processes for production of the DNA encoding rabbit IL-1 polypeptide are almost the same as the case of human IL-1 polypeptide.

The operations and conditions in the individual step of the processes to be described hereinbelow are well known in the art, and the processes of this invention are never limited to these specific procedures.

(1) Preparation of human IL-1 mRNA

Step a: Human IL-1 mRNA can be obtained, for example from human leukemia cells by the following method.

Human leukemia cells are seeded at a cell density of $1 \times 10^5$ to $5 \times 10^6$ cells/ml, and they are cultivated with an inducer(s) for differentiation into macrophage-like cells. The amount of the inducer(s) varies depending upon its type, kind of the leukemia cells, conditions of cultivation and so on. In the case of using the inducer(s) as described below, generally its final concentration is preferably about 100 to 2,000 ng/ml. The cultivation is carried out at 35° to 38° C., preferably about 37° C. in a humidity of about 90 to 100% in air containing about 5 to 10% of carbon dioxide for about 24 to 72 hours.

Human leukemia cells which can be used for the above step are all of human leukemia cells which are differentiated into macrophage-like cells by stimulating with the inducer. Examples include HL-60 cell (ATCC, CCL240), THP-1 cell, Mono-1-207 cell, and primary cells obtained from patients with leukemia.

As an inducer for differentiation, diterpenes such as phorbol esters, mezerein and retinoic acid can be used.

Various culture media suitable for the cultivation of mammalian cells can be used as the culture medium. Examples include RPMI-1640, Eagle's MEM medium and Dulbecco's modified MEM medium [for the compositions of the above media, see for example, "Cell Cultivation Manual" edited by Y. Sohmura, Kodansha (1982); and J. Paul "Cell and Tissue Culture", E. & S. Livingstone Ltd. (1970)]. Preferably, animal serum, such as fetal bovine serum or calf serum, is added to the culture medium in an amount of about 1 to 20%.

The following experiments will be made after confirming that leukemia cells are differentiated into macrophage-like cells, and get adherent to a dish.

However, in the case of using human macrophages collected from lung, blood, abdomen, placenta, spleen and other tissue, the differentiation step as mentioned above can be omitted.

Step b: After the cultivation as above, the culture medium and non-adherent cells are removed by suction. Then, the medium containing an inducer(s) for synthesis of IL-1 (for example, endotoxin derived from a gram-negative bacterium, a diterpene such as phorbol esters and mezerein) and a protein synthesis inhibitor (for example, cycloheximide) is added into the dish, and the cultivation is further continued for 3 to 8 hours to accumulate IL-1 mRNA in the macrophages. The amount of the endotoxin is generally about 0.1 to 1000 micrograms/ml (final concentration; the same as hereinbelow), preferably about 1 to 100 micrograms/ml. The amount of a phorbol ester is about 1 to 2000 ng/ml. The amount of cycloheximide is preferably 0.1 to 50 micrograms/ml.

After the cultivation, total RNA is extracted from the cells by a customary method, for example the method of Chirgwin et al. [Biochemistry, 18, 5294 (1979)], and then by affinity column chromatography on oligo(dT)-cellulose or poly(U)-Sepharose, or by a batch method, a fraction containing poly(A)mRNA is separated. An enriched mRNA fraction with human IL-1 mRNA can be obtained by acid-urea agarose gel electrophoresis or sucrose density gradient centrifugation of the poly-(A)mRNA fraction.

To confirm that the resulting mPNA fraction is the desired one containing mRNA encoding human IL-1 polypeptide, the mRNA is made to translate into a protein and its biological activity is examined. This can be carried out, for example, by injection it into the oocytes of *Xenopus laevis* or by applying it to a suitable protein synthesizing system, such as reticulocyte lysate or wheat germ cell-free protein synthesizing system and by confirming that the translated protein has IL-1 activity.

(2) Cloning of Human IL-1 cDNA

Step c The mRNA fraction obtained in the above (1) is used as a template and an oligo(dT) is used as a primer in order to synthesize a sscDNA by using reverse transcriptase (for example, that derived from avian myeloblastosis virus (AMV)) in the presence of dATP, dGTP, dCTP and dTTP. Then, the sscDNA is used as a template, and a dscDNA is synthesized by using reverse transcriptase on *E. coli* DNA polymerase I (large fragment).

Steps d and e: The resulting dscDNA is inserted, for example, into the restrictor endonuclease PstI cleavage site of plasmid pBR322 by a conventional method, for example the poly(dG)-poly(dC) homopolymer extension method (Nelson, T. S. "Methods in Enzymology", 68, 41 (1979), Academic Press Inc., New York). The resulting recombinant plasmids are introduced into a host such as *E. coli* X1776 in accordance with the method of Cohen et al. [Proc. Natl. Acad. Sci., USA, 69, 2110 (1972)] to transform it, and by selecting tetracycline-resistant colonies, a cDNA (colony) library is prepared.

Step f: To select the desired clones harboring recombinant plasmids containing a cDNA insert encoding human IL-1 polypeptide, the following methods will be used.

If a suitable DNA fragment, for example a cDNA fragment or a chemically synthesized DNA fragment corresponding to an animal (but not human) IL-1 polypeptide, can be previously obtained, the above cDNA library is subjected to colony hybridization assay [Hanahan, D., et al., Gene, 10, 63 (1980)] by using the above DNA fragment labelled with $^{32}P$ as a probe, and the desired clones harboring recombinant plasmids containing a cDNA insert having a nucleotide sequence(s) complementary to the DNA probe used are selected.

If such a suitable IL-1 DNA probe as above cannot be obtained, the desired clones are screened by colony hybridization using induction-plus and induction-minus probes and by mRNA hybridization-translation assay, for example according to the procedures as described below.

A $^{32}P$-labelled cDNA is synthesized using the mRNA fraction containing human IL-1 mRNA obtained in the above (1) as a template and used as an induction-plus probe. Separately, by using as a template a mRNA fraction obtained by the same procedure as described in the above (1) except that the non-induced macrophages are used as a starting material, a $^{32}P$-labelled cDNA is synthesized. This $^{32}P$-labelled cDNA is used as an induction-minus probe. From the above cDNA library, there are selected plasmid clones which are strongly hybridized with the induction-plus probe, but not hybridized with the induction-minus probe.

The A mRNA hybridization-translation assay is carried out in order to confirm that the selected clones harbor a cDNA insert encoding human IL-1 polypeptide. The plasmid DNAs are isolated from the above selected clones, converted into a single-stranded DNA by heating or alkali treatment, and fixed onto nitrocellulose filters. The mRNA fraction containing human IL-1 mRNA obtained according to the method as mentioned in the above (1), is added to the filters to hybridize with the fixed DNA. Then, the hybridized mRNA is eluted and recovered. The recovered mRNA is injected into oocytes of *Xenopus laevis* to determine whether the recovered mRNA encodes human IL-1 polypeptide.

The above methods give transformants harboring a recombinant plasmid having a cDNA fragment containing a nucleotide sequence complementary to the human IL-1 mRNA.

When the obtained cloned cDNAs do not contain whole coding region of human IL-1 polypeptide, cDNAs of a larger size are selected by screening the cDNA library using as a probe the cloned cDNA fragment from the transformant selected as above.

The cloned cDNA encoding a polypeptide containing the amino acid sequence of human IL-1 polypeptide can be proved finally by analyzing the nucleotide sequence of some of the resulting cloned cDNA fragments in accordance with, for example the Maxam-Gilbert method [Proc. Natl. Acad. Sci., USA, 74, 560 (1977)] or the dideoxy method using a M13 phage [Sanger, F., et al., Proc. Natl. Acad. Sci., USA, 74, 5463 (1977), and Messing, J., Methods in Enzymology, 101, 20 (1983)].

Step g (Modification): If desired, the cloned cDNA obtained as above can be modified by techniques known per se to form the DNA having and/or containing a nuclectide sequence deleted one or more codons and/or replaced with other codon(s) or degenerative codon(s).

Modification is carried out, for example, by cleaving the DNA with suitable restriction endonuclease(s) and splitting off one or more codons with suitable exoncleases and/or endonucleases singly or in combination, followed by replacing with degenerative condons, for example, those synthesized chemically by the phosphotriester method [Ohtsuka, E., et al., Heterocycles, 15, 395 (1981)], or by ligation without any supplement of codons to prepare DNA having one or more codons deleted.

[II] Polypeptides

The DNAs prepared in the above [I] are adequately inserted into an expression vector, and a host is transformed with said expression vector. Thereafter, the transformed host is cultivated to produce the desired polypeptide.

(A) Designation of polypeptides

The polypeptide produced by using a DNA derived from human IL-1 gene or cDNA is a polypeptide having an amino acid sequence represented by the formula [I-1] shown in the attached Table 1-1, wherein one to sixteen, preferably one to fifteen, amino acid residues at the N-terminus and/or one to seven, preferably one to five, amino acid residues at the C-terminus may be deleted.

Besides, the polypeptide produced by using a DNA derived from rabbit IL-1 gene or cDNA is a polypeptide having an amino acid sequence represented by the formula [A-1] show in the attached Table 3-1.

Preferred polypeptides of this invention are as follows:

(1) a polypeptide having an amino acid sequence represented by the formula [I-1], (2) a polypeptide having an amino acid sequence represented by the formula [I-1] in which two amino acid residues at the N-terminus are deleted, (3) a polypeptide having an amino acid sequence represented by the formula [I-1] in which ten amino acid residues at the N-terminus are deleted.

(4) a polypeptide having an amino acid sequence represented by the formula [I-1] in which fourteen or fifteen amino acid residues at the N-terminus are deleted, (5) a polypeptide having an amino acid sequence represented by the formula [I-1] in which four amino acid residues at the C-terminus are deleted, (6) a polypeptide having an amino acid sequence represented by the formula [I-1] in which five amino acid residues at the C-terminus are deleted, (7) a polypeptide having an amino acid sequence represented by the formula [I-1] in which fifteen amino acid residues at the N-terminus and four amino acid residues at the C-terminus are deleted, and (8) a polypeptide having an amino acid sequence represented by the formula [A-1].

It should be understood that the polypeptides of this invention include the following polypeptides:

a polypeptide possessing IL-1 activity, a polypeptide possessing IL-1 activity which is derived from human or rabbit IL-1 gene or cDNA, a polypeptide produced by cultivating a host transformed with an expression vector having the DNA of this invention inserted hereinto, a human or rabbit IL-1 polypeptide, a modified polypeptide of human IL-1 polypeptide, a degrated substance of human or rabbit IL-1 polypeptide in the host, a polypeptide which has at least a highly homologous portion(s) between human IL-1 polypeptide and rabbit IL-1 polypeptide.

(B) Production of Polypeptides

Processes for the production of the polypeptides of this invention will be described hereinbelow.

According to this invention, a human IL-1 polypeptide or its modified polypeptide and a rabbit IL-1 polypeptide (hereinafter, whole of these polypeptides are occasionally referred to merely as "the polypeptide") can be produced by the following steps:

i) inserting a DNA having or containing a nucleotide sequence encoding the polypeptide into an expression vector, ii) introducing the recombinant vector into a host, iii) cultivating the host transformed with the recombinant vector to produce the polypeptide, iv) collecting the cultured cells and extracting the polypeptide produced from them, and v) purifying the polypeptide by conventional purifying methods for proteins.

If desired, the polypeptide produced through the above steps may be modifed (as step vi) to produce other polypeptides of this invention, or their derivatives or salts.

A detailed description will follow of the processes for producing the polypeptide by using a DNA encoding the polypeptide.

Step i An expression vector for production of the polypeptide can be obtained by inserting a cloned DNA encoding the polypeptide. All vectors which proliferate in microorganisms to be transformed can be used. Examples include plasmids (such as E. coli plasmid pBR322), phages (such as lambda phage derivatives), and viruses (such as SV40). They may be used singly or in combination, for example as a pBR322-SV40 hybrid plasmid. The site of insertion of the DNA can be properly selected. In other words, a suitable site of a suitable vector may be cleaved with a suitable restriction endonuclease(s) in a customary manner, and the cloned DNA of suitable length may be inserted into the cleavage site.

More specifically, an expression vector for production of the polypeptide (non-fused) is constructed by joining a DNA fragment containing the nucleotide sequence encoding the polypeptide in which the initiation codon ATG is added to the 5'-terminus and the termination codon(s) (TAA, TAG or TGA) is added to the 3'-terminus, down stream a DNA fragment with a suitable promoter and the Shine-Dalgarno sequence and inserting it into a vector. An expression vector for the production of the fused polypeptide may be constructed by inserting the DNA fragment having the nucleotide sequence encoding the polypeptide in which the termination codon is added to its 3'-terminus, into the vector so that the translational reading frame coincides with that of the structure gene to be fused.

Examples of the promoters are lac, trp, tac, phoS, phoA, $P_L$ and SV40 early promoters.

Step ii Transformants are obtained by introducing the expression vector into a host such as microorganism, animal or plant cell. For example, E. coli is transformed by the method of Cohen et al. [Proc. Natl. Acad. Sci., USA, 69, 2110 (1972)]. Then, by cultivating the transformant, the polypeptide or the polypeptide with a methionine at its N-terminus is produced. The product can be accumulated either in the cytoplasm or in the periplasm of the host cell depending upon the method of constructing the expression vector. To cause the polypeptide to be secreted in the periplasm, one can construct an expression vector by using a gene coding for a secretory protein, such as an alkaline phosphatase gene (phoA) or a phosphate binding protein gene (phoS), and joining the DNA encoding the polypeptide in the correct translational reading frame into the above gene at a suitable site following a DNA region encoding the signal peptide.

Steps iii and iv The resulting transformant is cultivated under suitable conditions for the transformant until the polypeptide desired is fully produced. Then, the polypeptide is extracted from the culture. When the produced polypeptide is accumulated in the cytoplasm, the host cells are destroyed by lysozyme digestion and freezing and thawing or sonication or by using a French press, and then centrifuged or filtered to collect the extract. When it is accumulated in the periplasm, it can be extracted, for example, by the method of Willsky et al. [J. Bacteriol., 127, 595 (1976)].

Step v The polypeptide so obtained can be purified by conventional purifying methods for proteins, for example by combinations of salting out, ultrafiltration, dialysis, ion exchange chromatography, gel filtration, electrophoresis, affinity chromatography, etc.

By the foregoing processes, the polypeptide and/or the polypeptide with a methionine at the N-terminus of the polypeptide can be produced.

[III] Modification of polypeptides

Substances resulting from modification of the polypeptide include polypeptides resulting from addition of an amino acid or a peptide (consisting of two or more amino acids) to the N-terminus and/or C-terminus of the polypeptide; polypeptides resulting from deletion of one or more amino acids from the polypeptide; polypeptides resulting from change of asparagine or glutamine residue into aspartic acid or glutamic acid residue, respectively, or from change of aspartic acid or glutamic acid residue into asparagine or glutamine residue, respectively, and further include derivatives of the polypeptides, such as esters, acyl derivatives or acid amides, which are formed by using a functional group in the molecule, an amino residue of the N-terminus or a carboxy residue of the C-terminus, and their salts formed by using amino residues or carboxy residues with, for example, sodium hydroxide, potassium hydroxide, arginine, caffein, procaine, hydrochloric acid, gluconic acid and so on.

Such a modification or preparation of derivatives of the polypeptide are carried out by the techniques known per se, for example, according to the method as described in "Chemical Modification of Proteins" by Means, G. E. and Feeney, R. E., Holden-Day, Inc., California (1971).

The polypeptide of this invention may exist as its aggregate, or may also be changed in the host or in the course of separation. In case that cysteine residue is a component of a polypeptide of this invention, this residue may constitute S—S bond between the molecules. These changed polypeptides are also included in the present invention.

In case of transformation of a host with a vector inserted with a DNA encoding human or rabbit IL-1 precursor or a DNA containing a region upstream a nucleotide sequence encoding mature human or rabbit IL-1, the transformed host may occasionally produce a precursor polypeptide, a polypeptide combined with a polypeptide corresponding to the upstream DNA at the N-terminus of the mature polypeptide with or without the mature polypeptide. These polypeptides are also included in this invention.

[IV] Chemical and Physical Properties of Polypeptides:

Chemical and physicochemical properties of mature human IL-1 polypeptide and its modified polypeptides will be described below.

(A) Procedures for analyses

Molecular weight

The molecular weight was measured by sodium dodecyl sulfate (SDS)-polyacrylamide gel (gel concentration; 12.5%) electrophoresis.

A sample solution was mixed with an equal volume of 0.125M Tris-HCl (pH 6.8) buffer containing 4% SDS, 10% 2-mercaptoethanol, 20% glycerol and 0.02% bromophenol blue, followed by standing for 30 minutes at room temperature. The mixture was subjected to SDS-polyacrylamide gel electrophoresis under the conditions of 200 volts for 3 hours using 0.2M glycine solution containing 25 mM Tris and 0.1% SDS as an electrophoresis electrolyte. After electrophoresis, each migration lane was separated by cutting, and a lane was stained with Coomassie Brilliant Blue C-250 to detect proteins. Then, another lane was cut into strips of 2 mm-width, and each strip was immersed into RPMI-1640 medium containing 5% fetal bovine serum or a 1% ammonium bicarbonate solution to elute the polypeptide in the gel strip. The eluate from each gel strip was subjected to IL-1 activity assay according to the method as mentioned in Example 1.

As molecular weight marker proteins, the following proteins were used; phosphorylase-b (MW: 94,000), bovine serum albumin (MW: 67,000), ovalbumin (MW: 43,000), carbonic anhydrase (MW: 30,000), soybean trypsin inhibitor (MW: 20,100) and alpha-lactalbumin (MW: 14,400).

Determination of N-terminal amino acid and amino acid sequence

N-terminal amino acid was determined by dansylation method [Gray, W. R., Methods in Enzymol., Vol XI, p139 (1967)].

The sample solution (100 microliters) was mixed with 10 microliters of 10% SDS, 100 microliters of N-ethylmorpholine and 50 microliters of dansyl chloride solution (5 mg/ml in acetone), and incubated at 37° C. for 1 hour. Then, 2 ml of acetone was added to the reaction mixture, and the resulting precipitate was collected by centrifugation. After washing with 80% acetone, the precipitate was dried in vacuo. And then it was dissolved in 100 microliters of 6N HCl, and it was heated at 105° C. for 5 to 18 hours in a glass tube sealed under the condition of vacuo. The resulting dansylated amino acid was extracted by water-saturated ethyl acetate from the sample dried in vacuo. The dansylated amino acid was identified by two dimentional thin layer chromatography using a polyamine sheet (Cheng-Chin Trading Co., Taiwan) according to the method of Wood and Wang [Biochem. Biophys. Acta, 133, 369 (1967)].

N-terminal amino acid sequence was determined by the Edman degradation method [Arch. Biochem. Biophys., 22, 475 (1949)].

A phenylthiohydantoin-amino acid derived from an N-terminal amino acid by the Edman degradation method was identified by high-performance liquid chromatography using a column of TSK-gel ODS-120A (Toyo Soda Kogyo, Japan). These procedures were serially repeated to determine a newly formed N-terminal amino acid derivative sequentially.

Determination of C-terminal amino acid sequence

C-terminal amino acid sequence was determined by the enzymatic method using carboxypeptidases.

The sample was digested with carboxypeptidase-A and carboxypeptidase-Y. The free amino acids released were identified and determined quantitatively by a micro-amino acid analyzer (Shimadzu Seisakusho, Japan) at appropriate intervals of the enzymatic digestion.

Isoelectric point

An isoelectric point was determined by isoelectrofocusing gel electrophoresis at 5 watt for 3 hours using a 5% polyacrylamide flat gel with a pH gradient created with Pharmalyte (Pharmacia, Sweden).

(B) Chemical and physiocochemical properties:

Chemical and physicochemical properties of mature human IL-1 polypeptide and its modified polypeptides were summarized in the following Tables (a), (b) and (c).

In Tables (a), (b) and (c), mature human IL-1 polypeptide and its modified polypeptides are as follows;

Mature human IL-1 polypeptide is a polypeptide obtained in Example 5-(2) which corresponds to the amino acid sequence from the amino acid No. 113 to the amino acid No. 271 in Table 5.

IL-1(157) is a polypeptide obtained in Example 6-(2) which corresponds to the amino acid sequence from the amino acid No. 115 to the amino acid No. 271 in Table 5.

IL-1(149) is a polypeptide obtained in Example 7-(2) which corresponds to the amino acid sequence from the amino acid No. 123 to the amino acid No. 271 in Table 5.

IL-1(144) is a polypeptide obtained Example 8-(2) which corresponds to the amino acid sequence from the amino acid No. 127 or 128 to the amino acid No. 271 in Table 5.

IL-1(155-C) is a polypeptide obtained in Example 10-(2) which corresponds to the amino acid sequence from the amino acid No. 113 to the amino acid No. 267 in Table 5.

TABLE (a)

| item | Properties of mature human IL-1 polypeptide |
|---|---|
| | mature human IL-1 polypeptide |
| molecular weight | 18,000 ± 500 |
| isoelectric point | pI 5.3 ± 0.3 |
| N-terminal amino acid sequence | Ser—Ser—Pro—Phe—Ser—Phe—Leu—Ser—Asn—Val—Lys—Tyr—Asn—Phe—Met—Arg—Ile—Ile—Lys—Tyr—Glu—Phe—Ile—Leu—Asn—Asp—Ala—Leu—Asn—Gln— |
| C-terminal amino acid sequence | —Asx—Glx—Ala |

TABLE (b)

| item | Properties of IL-1(157), IL-1(149) and IL-1(144) | | |
|---|---|---|---|
| | IL-1(157) | IL-1(149) | IL-1(144) |
| molecular weight | 17,700 ± 300 | 16,100 ± 300 | 16500 ± 300 |
| N-terminal amino acid | Pro—Phe—Ser—Phe—, | Lys—Tyr—Asn—Phe—Met—, | Y—Ile—Ile—Lys—Tyr—, |
| C-terminal amino acid | From each of the above three polypeptide, the following amino acids were released and identified; Ala, Glx, Asx, Leu, Ile, Phe, | | |

TABLE (c)

| item | Properties of IL-1(155-C) |
|---|---|
| | IL-1(155-C) |
| molecular weight | about 17,500 |
| N-terminal amino acid | Ser—Ser—Pro—Phe—Ser— |
| C-terminal amino acid | —Glx—Ile—Leu |

In the above tables, Glx represents Glu or Gln, Asx represents Asp or Asn, and Y represents Arg or Met-Arg.

[V] Formulation and use

For formulating the polypeptides or substances of this invention, they may be in the form of a solution or a lyophilized product. From the standpoint of long-term stability, they are desirably in the form of lyophylized products. It is preferred to add vehicles or stabilizers to the preparations. Examples of the stabilizers include albumin, globulin, gelatin, protamine, protamine salts, glucose, galactose, xylose, mannitol, glucuronic acid, trehalose, dextran, hydroxyethyl starch, and nonionic surface-active agents (such as polyoxyethylene fatty acid esters, polyoxyethylene alkyl ethers, polyoxyethylene alkyl phenyl ethers, polyoxyethylene sorbitan fatty acid esters, polyoxyethylene glycerin fatty acid esters, polyoxyethylene hardened castor oil, polyoxyethylene castor oil, polyoxyethylene polyoxypropylene alkyl ethers, polyoxyethylene polyoxypropylene block copolymer, sorbitan fatty acid esters, sucrose fatty acid esters and glycerin fatty acid esters).

The polypeptides or substances of this invention are useful as an antitumor or antiinfectious agent because they regress tumors transplanted in animals, and relieve animals from fatal microbial infections.

Such preparations are preferably administered parenterally or topically. Parenteral routes such as intravenous, subcutaneous and intramuscular routes are used when tumor cells or pathogens extend over a wide range of body, or when prevention of metastasis of tumors or microbial infections is intended. Against local tumor tissues or local infections, local administration is preferred. The dosage varies depending upon the type and size of tumors or infections, the condition of the patient and the route of administration. An antiinflammatory agent such as indomethacin may be co-administered.

[VI] Examples

The following examples illustrate this invention more specifically. It should be understood however that the invention is in no way limited to these examples.

For better understanding of the following examples, FIGS. 1 to 10 and Tables 5–8 are attached to the present specification.

Example 1 Cloning and sequencing of cDNA encoding human IL-1

(1) Preparation of human IL-1 mRNA from human promyelocytic leukemia cells (HL-60)

HL-60 cells were seeded in Petri dishes (8 cm in diameter) at a cell density of $1 \times 10^7$ cells/dish in 10 ml of RPMI-1640 medium containing 10% fetal bovine serum with 500 ng/ml phorbol-12-myristate-13-acetate and 500 ng/ml retinoic acid as a differentiation inducer. After cultivation at 37° C. in a fully humidified atmosphere containing 5% carbon dioxide for 2 days, the culture medium and non-adherent cells were removed by suction. Into the dishes to which the differentiated cells adhered, 10 ml of RPMI-1640 medium containing 10% fetal bovine serum supplemented with 10 micrograms/ml endotoxin (lipopolysaccharide derived from *E. coli*, which is hereinafter referred to as "LPS") as an inducer and 1 microgram/ml cycloheximide (protein synthesis inhibitor) was added and further cultivated for 5 hours. The culture medium was removed by suction, and the induced cells adhered to the dishes were lysed and homogenized in a 6M guanidinium thiocyanate solution containing 0.5% sodium N-laurcyl sarcosinate, 5 mM sodium citrate and 0.1M 2-mercaptoethanol. The homogenate was loaded on a 5.7M cesium chloride solution containing 0.1M EDTA, and centrifuged for 20 hours at 26,500 rpm using an ultracentrifuge (RPS27-2 rotor, Hitachi Koki, Japan) to obtain a total RNA fraction as pellets. The pellets were dissolved in a small amount of a 7M urea solution containing 0.35M NaCl, 30 mM Tris-HCl (pH 7.4) and 20 mM EDTA, and recovered by precipitation from ethanol. From $1.5 \times 10^8$ cells of HL-60, 1.7 mg of the total RNA was obtained. The total RNA fraction was dissolved in 2 ml of 10 mM Tris-HCl (pH 7.4) buffer containing 1 mM EDTA (hereinafter, referred to as "TE solution"), and the solution was heated at 65° C. for 5 minutes. A NaCl solution was added to a final concentration of 0.5M, and the solution was applied onto a column of oligo(dT)-cellulose previously equilibrated with the TE solution containing 0.5M NaCl. Poly(A)mRNA was eluted from the column with the TE solution in an yield of about 75 micrograms.

The poly(A)mRNA was injected into the occytes of *Xenopus laevis* at a dose of about 150 ng/oocyte, and the 10 oocytes were incubated in 100 microliters of Barth's medium at 22° C. for 24 hours. The oocytes were homogenized and centrifuged. The supernatant was subjected to the assay of IL-1 activity according to the method as mentioned below.

The RPMI-1640 medium containing 5% fetal bovine serum is used as a medium. A sample is diluted with the medium into an appropriate concentration. Fifty microliters of the dilution is added into each well of a 96 well multi-well plate (Flow Labs., USA). Furthermore, 50 microliters of 50 micrograms/ml phytohemagglutinin-P (Difco Labs., USA) and 100 microliters of thymocyte suspension ($1 \times 10^7$ cell/ml) collected from C3H/He (6–10 week old) mice are added into the well. The plate is incubated at 37° C. in a fully humidified atmosphere containing 5% carbon dioxide. After incubation for 2 days, 1 microcurie of $^3$H-thymidine is added into each well and the plate is further incubated for 18 hours. The thymocyte cells are collected onto a Harvester Filter (Flow Labs.) using a Titertek Cell Harvester (Flow Labs.). The radioactivity of $^3$H-thymidine incorporated into the cells is counted. The LAF (lymphocyte activating factor) activity is determined with the augmentation of $^3$H-thymidine incorporation by comparison with the $^3$H-thymidine incorporation of a control using the medium instead of a test sample.

The above method was used as an assay for the IL-1 activity in all of the following examples.

A 320-fold diluted solution of the supernatant prepared as above showed an incorporation of about 15,000–18,000 cpm of $^3$H-thymidine. It indicates that the poly(A)mRNA preparation contains IL-1 mRNA.

(2) Synthesis of cDNA

Complementary DNA was synthesized according to the method of Gubler and Hoffman [Gene, 25, 263 (1983)] using the poly(A)mRNA obtained in the above (1) as a template.

Six micrograms of the poly(A)mRNA were dissolved in 6 microliters of distilled water, and then thereto was added 0.6 microliter of 100 mM methylmercury hydroxide solution. After standing at room temperature for 10 minutes, 1.7 microliters of 500 mM 2-mercaptoethanol solution containing 20 units of ribonuclease inhibitor (RNasin ®, Product of Promega Biotech, USA) was added to the mixture. After standing at room temperature for 5 minutes, 32 microliters of 50 mM Tris-HCl (pH 8.3) buffer containing 10 mM $MgCl_2$, 1.25 mM dGTP, 1.25 mM dATP, 1.25 mM dTTP, 0.5 mM dCTP, 170 nM alpha-$^{32}$P-dCTP (specific radioactivity, 750 Ci/mmole), 4 micrograms of oligo(dT)$_{12-18}$ and 120 units of AMV reverse transcriptase was added to the mixture and it was incubated at 42° C. for 60 minutes. The reaction was stopped by adding EDTA. The reaction mixture was extracted with phenol/chloroform (1:1), and ammonium acetate was added to the aqueous phase to a final concentration of 2.5M. The resulting sscDNA-mRNA hybrid was recovered from the aqueous phase by precipitation from ethanol. The sscDNA-mRNA hybrid precipitate was dissolved in 100 microliters of 20 mM Tris-HCl (pH 7.5) buffer containing 5 mM $MgCl_2$, 10 mM $(NH_4)_2SO_4$, 100 mM KCl, 0.15 mM beta-nicotinamide-adenine dinucleotide, 5 micrograms of bovine serum albumin, 0.04 mM of each of four deoxyribonucleotide triphosphates, dGTP, dATP, dTTP and dCTP, 1.25 units of *E. coli* ribonuclease H and 24 units of *E. coli* DNA polymerase I. The reaction mixture was incubated at 12° C. for 60 minutes, and then 2.5 units of *E. coli* DNA ligase was added, and it was further incubated at 22° C. for 60 minutes to synthesize a dscDNA. The reaction was stopped by adding EDTA. The dscDNA was extracted with phenol/chloroform and recovered by precipitation from ethanol as mentioned above.

(3) Preparation of oligo(dC)-tailed cDNA

The dscDNA obtained as above was dissolved in 100 microliters of 100 mM sodium cacodylate (pH 7.2) buffer containing 2 mM $CoCl_2$, 0.2 mM dithiothreitol, 0.1 mM alpha-$^{32}$P-dCTP (specific radioactivity, 1 Ci/mmole) and 10 units of terminal deoxynucleotidyl transferase, and incubated at 37° C. for 30 minutes to permit the addition of oligo(dC) tails to the 3'-termini of dscDNA.

The reaction was stopped by adding EDTA. The oligo(dC)-tailed dscDNA was extracted with phenol/chloroform, and recovered by precipitation from ethanol. The oligo(dC)-tailed dscDNA was dissolved in 10 mM Tris-HCl (pH 7.4) buffer containing 1 mM EDTA and 100 mM NaCl so that it contained 2 micrograms of the oligo(dC)-tailed dscDNA per ml.

(4) Construction of recombinant plasmids

Oligo(dC)-tailed pBR322 DNA (product of Bethesda Res. Labs. Inc., USA) and the oligo(dC)-tailed dscDNA obtained in the above (3) were dissolved in 10 mM Tris-HCl (pH 7.4) buffer containing 1 mM EDTA and 100 mM NaCl so that it contained 1.5 micrograms and 0.09 microgram, respectively, in a total volume of 1.5 ml.

The mixture was incubated sequentially at 65° C. for 10 minutes, at 57° C. for 2 hours and at 45° C. for 2 hours to perform annealing and to construct recombinant plasmids.

(5) Selection of transformants

E. coli X1776 strain was transformed with the recombinant plasmids obtained as above.

Specifically, E. coli X1776 was cultivated at 37° C. in 20 ml of L broth (composition: 10 g tryptone, 5 g yeast extract, 5 g NaCl and 1 g glucose per liter, pH 7.2) supplemented with 100 micrograms/ml of diaminopimelic acid and 40 micrograms/ml of thymidine until the turbidity at 600 nm reached 0.5. The cells were collected by centrifugation at 4° C., and washed with 10 ml of 10 mM Tris-HCl (pH 7.3) buffer containing 50 mM CaCl$_2$. The cells were resuspended in 2 ml of the same buffer as used above, and allowed to stand at 0° C. for 5 minutes. To 0.2 ml of the cell suspension was added 0.1 ml of the recombinant plasmid solution obtained as above. The mixture was allowed to stand at 0° C. for 15 minutes and then maintained at 42° C. for 2 minutes. Then, 0.5 ml of the supplemented L broth as used above was added, and cultivation was carried out with shaking for 1 hour. An aliquot of the culture was taken, spread on the supplemented L broth agar plate containing 15 micrograms/ml of tetracycline, and cultivated at 37° C. for about 12 hours. A cDNA library was prepared by selecting transformants resistant to tetracycline.

(6) Cloning

Transformants harboring the recombinant plasmids containing cDNAs encoding human IL-1 were selected from the cDNA library obtained in the above (5), by the colony hybridization assay using the cloned cDNA encoding rabbit IL-1 obtained in Example 2, as a probe.

Specifically, the cloned cDNA (about 1.1 kbp) encoding rabbit IL-1 was isolated from the recombinant plasmid pRL15 as shown in Example 2-(6) by digestion with a restriction endonuclease PstI, and labelled with $^{32}$P. This labelled cDNA was used as a probe for screening the cDNA library to select transformants having a plasmid containing cDNA encoding human IL-1 by the colony hybridization assay as mentioned above.

Five clones having cDNA which could strongly be hybridized with the labelled probe were selected from about 20,000 clones. Furthermore, 2 clones harboring the recombinant plasmids containing cDNA of 2 kbp or more in size were selected, and they were subjected to the mRNA hybridization translation assay. The plasmid DNA was extracted from each of the selected clones and fixed to nitrocellulose filters after heat denaturation. The poly(A)mRNA fraction containing human IL-1 mRNA obtained in the above (1) was added to the filters and incubated at 50° C. for 5 hours to perform hybridization. The hybridized mRNA was recovered and injected into the oocytes of Xenopus laevis to determine whether the recovered mRNA was IL-1 mRNA. By this test, it was confirmed that each of these 2 clones contained cDNA which could strongly be hybridized with human IL-1 mRNA.

Out of these 2 clones, one clone harboring a recombinant plasmid containing cDNA of about 2.1 kbp in size was selected for sequencing the cloned cDNA (designated plasmid No. pHL4; clone No. X1776/pHL4).

(7) Determination of the nucleotide sequence of the cloned cDNA

The transformant (X1776/pHL4) selected in the above (6) was cultivated in L broth supplemented with diaminopimelic acid and thymidine. The cells were treated in accordance with the method of Wilkie et al. [Nucleic Acids Res., 7, 859 (1979)] to obtain a plasmid DNA. The plasmid DNA was cleaved with restriction endonuclease PstI, and purified to obtain a cloned cDNA insert. The cloned cDNA was further cleaved with a single or two kinds of the following restriction endonucleases, SacI, RsaI, HindIII, HincII, Fnu4HI, HinfI, BalI and EcoRI. The resulting cDNA fragments being about 150–700 bp in size were isolated and used for determination of their nucleotide sequences.

The determination of nucleotide sequences were done by the dideoxy method according to the text of "M13 cloning and sequencing handbood (Amersham International plc)" by using M13 sequencing kit (Amersham International plc), and M13mp18 and M13mp19 (product of P-L Biochemicals) as a cloning vector.

Table 5 shows the nucleotide sequence encoding human IL-1 and the amino acid sequence deduced from the nucleotide sequence, wherein the codon of base No. 1 to base No. 3 is an initiation codon ATG and the codon of base No. 814 to base No. 816 is a stop codon TAG.

The nucleotide coding for human IL-1 encodes its precursor polypeptide consisting of 271 amino acids (amino acid No. 1–271 in Table 5). Mature human IL-1 polypeptide is a polypeptide corresponding to the 159 amino acids from the C-terminus of its precursor, which is coded in the nucleotide sequence from base No. 337 to base No. 813 in the Table 5.

Example 2 Cloning and sequencing of cDNA encoding rabbit IL-1

(1) Preparation of rabbit IL-1 mRNA from rabbit alveolar macrophage cells

Rabbits weighing about 2.5–3.0 kg were intravenously injected with killed dried cells of Propionibacterium acnes at a dose of 100 mg per rabbit, and sacrificed 8 days later. The lungs were repeatedly washed with phosphate buffered saline through a tube inserted into the trachea of the animals, and alveolar macrophages were collected. The alveolar macrophages were suspended in RPMI-1640 medium containing 10% fetal bovine serum, and seeded in Petri dishes (8 cm in diameter) at a cell density of $1 \times 10^7$ cells/dish. They were pre-incubated at 37° C. in a fully humidified atmosphere containing 5% carbon dioxide. After 1 hour cultivation, LPS, TPA (phorbol-12-myristate-13acetate) and cycloheximide were added to the dishes so that their final concentrations became 10 micrograms/ml, 10 ng/ml and 1 microgram/ml, respectively. The cultivation was further continued for 4 hours. The culture medium was removed by suction, and the macrophages adhered to the dishes were lysed and homogenized in a 6M guanidinium thiocyanate solution containing 0.5% sodium N-lauroyl sarcosinate, 5 mM sodium citrate and 0.1M 2-mercaptoethanol. The homogenate was loaded on a cushion of a 5.7M cesium chloride solution containing 0.1M EDTA, and centrifuged for 20 hours at 26,500 rpm using an ultracentrifuge (RPS27-2 rotor, Hitachi Koki) to obtain a total RNA fraction as pellets. The pellets were dissolved in a small amount of a 7M urea solution containing 0.35M NaCl, 20 mM Tris-HCl (pH 7.4) and 20 mM EDTA, and recovered by precipitation from ethanol. The total RNA fraction was dissolved in 2 ml of the TE solution, and the solution was heated at 65° C. for 5 minutes. A NaCl solution was added to a final concentration of 0.5M, and the solution was applied onto a column of ligo(dT)-cellulose previously equilibrated with the TE solution containing 0.5M NaCl. Poly(A)mRNA was eluted from the column with the TE solution. The poly(A)-mRNA was obtained in an yield of about 300 micrograms from $1.3 \times 10^9$ cells of rabbit alveolar macrophages.

The resulting poly(A)mRNA was subjected to agarose gel electrophoresis (gel concentration 1%, in the presence of 6M urea at pH 4) according to the method of Lehrach et al. [Biochemistry, 16, 4743 (1977)], and the poly(A)mRNA fraction containing rabbit IL-1 mRNA was recovered from the gel fraction corresponding to about 2.6–3.7 kb in size by the method of Gray et al. [Nature, 295, 503 (1982)] (hereinafter referred to as "enriched poly(A)mRNA"). About 34 micrograms of the enriched poly(A)mRNA were obtained from 200 micrograms of the poly(A)mRNA.

The enriched poly(A)mRNA was dissolved in distilled water at a concentration of 0.2 microgram per microliter, and the solution was injected into the oocytes of *Xenopus laevis* at a dose of about 50 nl per oocyte, and the ten oocytes were incubated in 100 microliters of the Barth's medium [J. B. Gurdon, J. Embryol. Exp. Morphol. 20, 401 (1968)] at 22° C. for 24 hours. The oocytes were homogenized and centifuged. The supernatant was subjected to assay of IL-1 activity.

Each of 100-fold and 400-fold dilutions of the supernatant prepared as above showed $^3$H-thymidine incorporation of 7,979 cpm and 2,187 cpm into the mouse thymocyte, respectively. It indicates that the enriched poly(A)mRNA preparation contains IL-1 mRNA.

(2) Synthesis of cDNA

Complementary DNA was synthesized according to the method of Gubler and Hoffman [Gene, 25, 263 (1983)] using the enriched poly(A)mRNA obtained in the above (1) as a template.

Four micrograms of the enriched poly(A)mRNA were dissolved in 50 microliters of 50 mM Tris-HCl (pH 8.3) buffer containing 10 mM MgCl$_2$, 10 mM dithiothreitol, 4 mM sodium pyrophosphate, 1.25 mM dGTP, 1.25 mM dATP, 1.25 mM dTTP, 0.5 mM dCTP, 170 nM alpha-$^{32}$P-dCTP (specific radioactivity, 750 Ci/m-mole), 5 micrograms of cligo(dT)$_{12-18}$ and 120 units of reverse transcriptase derived from AMV and incubated at 42° C. for 60 minutes. The reaction was stopped by adding EDTA. The reaction mixture was extracted with phenol/chloroform (1:1), and ammonium acetate was added to the aqueous phase to a final concentration of 2.5M. The resulting sscDNA-mRNA hybrid was recovered from the aqueous phase by precipitation from ethanol. The sscDNA-mRNA hybrid precipitate was dissolved in 100 microliters of 20 mM Tris-HCl (pH 7.5) buffer containing 5 mM MgCl$_2$, 10 mM (NH$_4$)$_2$SO$_4$, 100 mM KCl, 0.15 mM beta-nicotinamide-adenine dinucleotide, 5 micrograms of bovine serum albumin, 0.04 mM of each of four deoxyribonucleotide triphosphates, dGTP, dATP, dTTP, and dCTP, 12.5 units of *E. coli* ribonuclease H and 50 units of *E. coli* DNA polymerase I. The reaction mixture was incubated at 12° C. for 60 minutes, and further incubated at 22° C. for 60 minutes to synthesize a dscDNA. The reaction was stopped by adding EDTA. The dscDNA was extracted with phenol/chloroform and recovered by precipitation from ethanol as mentioned above.

(3) Preparation of cligo(dC)-tailed cDNA

The dscDNA obtained as above was dissolved in 100 microliters of 100 mM sodium cacodylate (pH 7.2) buffer containing 2 mM CoCl$_2$, 0.2 mM dithiothreitol, 0.1 mM alpha-$^{32}$P-dCTP (specific radioactivity, 1 Ci/m-mole) and 10 units of terminal deoxynucleotidyl transferase, and incubated at 37° C. for 30 minutes to permit the addition of oligo(dC) tails to the 3'-termini of dscDNA.

The reaction was stopped by adding EDTA. The oligo(dC)-tailed dscDNA was extracted with phenol/chloroform, and recovered by precipitation from ethanol. The oligo(dC)-tailed dscDNA was dissolved in 10 mM Tris-HCl (pH 7.4) buffer containing 1 mM EDTA and 100 mM NaCl so that it contained 2 micrograms of the oligo(dC)-tailed dscDNA per ml.

(4) Construction of recombinant plasmids

Oligo(dG)-tailed pBR322 DNA (Product of Bethesda Res. Labs. Inc., USA) and the oligo(dC)-tailed dscDNA obtained in the above (3) were dissolved in 10 mM Tris-HCl (pH 7.4) buffer containing 1 mM EDTA and 100 mM NaCl so that they were contained in 1.5 micrograms and 0.09 microgram, respectively, in a total volume of 1.5 ml.

The mixture was incubated sequentially at 65° C. for 10 minutes, at 57° C. for 2 hours and at 45° C. for 2 hours to perform annealing and to construct recombinant plasmids.

(5) Selection of transformants

*E. coli* X1776 strain was transformed with the recombinant plasmids obtained as above.

Specifically, *E. coli* X1776 was cultivated at 37° C. in 20 ml of L broth (composition: 10 g tryptone, 5 g yeast extract, 5 g NaCl and 1 g glucose per liter; pH 7.2) supplemented with 100 micrograms/ml of diaminopimelic acid and 40 micrograms/ml of thymidine until the turbidity at 600 nm reached 0.5. The cells were collected by centrifugation at 4° C., and washed with 10 ml of 10 mM Tris-HCl (pH 7.3) buffer containing 50 mM CaCl$_2$. The cells were resuspended in 2 ml of the same buffer as used above, and allowed to stand at 0° C. for 5 minutes. To 0.2 ml of the cell suspension was added 0.1 ml of the recombinant plasmid solution obtained as above. The mixture was allowed to stand at 0° C. for 15 minutes and then maintained at 42° C. for 2 minutes. Then, 0.5 ml of the supplemented L broth as used above was added, and cultivation was carried out with shaking for 1 hour. An aliquot of the culture was taken, spread on the supplemented L broth agar plate containing 15 micrograms/ml of tetracycline, and cultivated at 37° C. for about 12 hours. A cDNA library was prepared by selecting transformants resistant to tetracycline.

(6) Cloning

In order to screen the cDNA library for transformants which had a plasmid containing cDNA encoding rabbit IL-1, colony hybridization assay was conducted by the method of Hanahan and Meselson [Gene, 10, 63 (1980)] using a $^{32}$P-labelled induction-plus and induction-minus cDNA probe. Each of induction-plus and induction-minus $^{32}$P-labelled sscDNA probes was synthesized respectively by the method described in the above (2) using as a template the enriched poly(A)mRNA fraction which was fractionated by the acid-urea agarose gel electrophoresis from each of the alveolar macrophages induced with LPS, TPA and cycloheximide by the method described in the above (1) and of the non-induced alveolar macrophages. By this test, there were selected colonies of transformants harboring the recombinant plasmids which strongly hybridized with the induction-plus probe but did not hybridize with the induction-minus probe. From about 5,000 colonies, 648 colonies were selected.

Ten groups of the selected colonies (including 10 colonies in each group) were then subjected to mRNA hybridization-translation assay by the method described in T. Maniatis et al. (ed) "Molecular Cloning", 329 (1980), Cold Spring Harbor Lab. The plasmid DNAs were extracted from the each group, and linealized by digestion with restriction endonuclease EcoRI, and fixed to nitrocellulose filters after heat denaturation. The poly(A)mRNA fraction containing rabbit IL-1 mRNA obtained in the above (1) was added to the filter and incubated at 50° C. for 5 hours to perform hybridization. The hybridized mRNA was recovered and injected into the oocytes of Xenopus laevis to determine whether the recovered mRNA was rabbit IL-1 mRNA. As a result of this test, it was found that one group (designated H-1603) had plasmids containing cDNAs which strongly hybridized with the rabbit IL-1 mRNA (see FIG. 1-A). Each clone of the group H-1603 was further subjected to the mRNA hybridization-translation assay as above, and it was found that one clone was strongly hybridized with rabbit IL-1 mRNA (see FIG. 1-B). This selected clone was designated pRL15. The cDNA insert was cut out from the recombinant plasmid pRL15 by digestion with restriction endonclease PstI, and it was labelled with $^{32}$P. By using this $^{32}$P-labelled cDNA as a probe, 648 colonies selected as above were screened by colony hybridization assay again. As a result of this test, 8 clones were hybridized with the $^{32}$P-labelled cDNA probe.

(7) Determination of the nucleotide sequence of the cloned cDNA

The recombinant plasmid pRL15 was cleaved with restriction endonclease PstI, and purified to obtain a cloned cDNA insert. The cloned cDNA was further cleaved with a single or two kinds of the following restriction endonucleases, HaeIII, HincII, AccI, PvuII, AvaII and RsaI. The resulting cDNA fragments being about 100–600 bp in size were used for nucleotide sequence determination.

The determination of nucleotide sequences were done by the dideoxy method accoding to the text of "M13 cloning and sequencing handbook (Amersham International plc)", by using a M13 sequencing kit (Amersham International plc), and M13mp18 and M13mp19 (product of P-L Biochemicals) as a cloning vector.

Table 7 shows the nucleotide sequence and the amino acid sequence deduced from the nucleotide sequence encoding rabbit IL-1.

The codon of base No. 1 to base No. 3 is an initiation codon ATG, and the codon of base No. 802 to base No. 804 is a stop codon TAA. The DNA coding for rabbit IL-1 encodes its precursor polypeptide consisting of 267 amino acid residues (amino acid No. 1–267 in Table 7). Mature rabbit IL-1 polypeptide is a polypeptide corresponding to the 155 amino acids from the C-terminus of its precursor; which is coded in the nucleotide sequence from base No. 337 to base No. 801 in the Table 7.

Homology between the nucleotide sequences coding for human and rabbit IL-1 precursor polypeptides, and homology between the deduced amino acid sequences of human and rabbit IL-1 precursor polypeptides are shown in Table 8-1 and 8-2, respectively. Homologies in the nucleotide sequences and the amino acid sequences are about 79% and 64%, respectively.

Example 3 Cloning and sequencing of human genomic IL-1 gene

Human genomic IL-1 gene was screened from the human genomic library, HaeIII-AluI digested human DNA fragments inserted into bacteriophage Charon 4A, which was supplied by Dr. T. Maniatis, [Harvard University, Department of Biochemistry and Molecular Biology, USA; Lawn, R. M. et al., Cell 15, 1157 (1978)] by the plaque hybridization method of Benton and Davis [Science, 196, 180 (1977)] using as a probe the $^{32}$P-labelled DNA fragment as prepared below. From the recombinant plasmid pHL4 obtained in Example 1-(6), the DNA fragment of about 847 bp in size corresponding to the downstream from the base No. 5 in Table 5, was cut out by double digestion with restriction endonucleases BalI and HincII, and labelled with $^{32}$P by nick-translation method.

As a result, six phage clones containing the nucleotide sequence that strongly hybridized with the probe were isolated from the library of about 600,000 phage plaques. These clones were further screened for the clones which covered all the exons of human IL-1 gene by hybridization method using the $^{32}$P-labelled DNA fragment (about 1.1 kbp in size) cut out with restriction endonuclease HincII and HindIII from the cDNA insert of recombinant plasmid pHL4 obtained in Example 1-(6) as a probe. The above HincII-HindIII DNA fragment contains most of the 3'-noncoding region of human IL-1 cDNA. Out of clones selected as above, four clones were strongly hybridized with this probe. The recombinant phage DNA was isolated from each clone and characterized by restriction endonuclease mapping. One clone (λHL#4) was selected for nucleotide sequencing.

Figure 2:
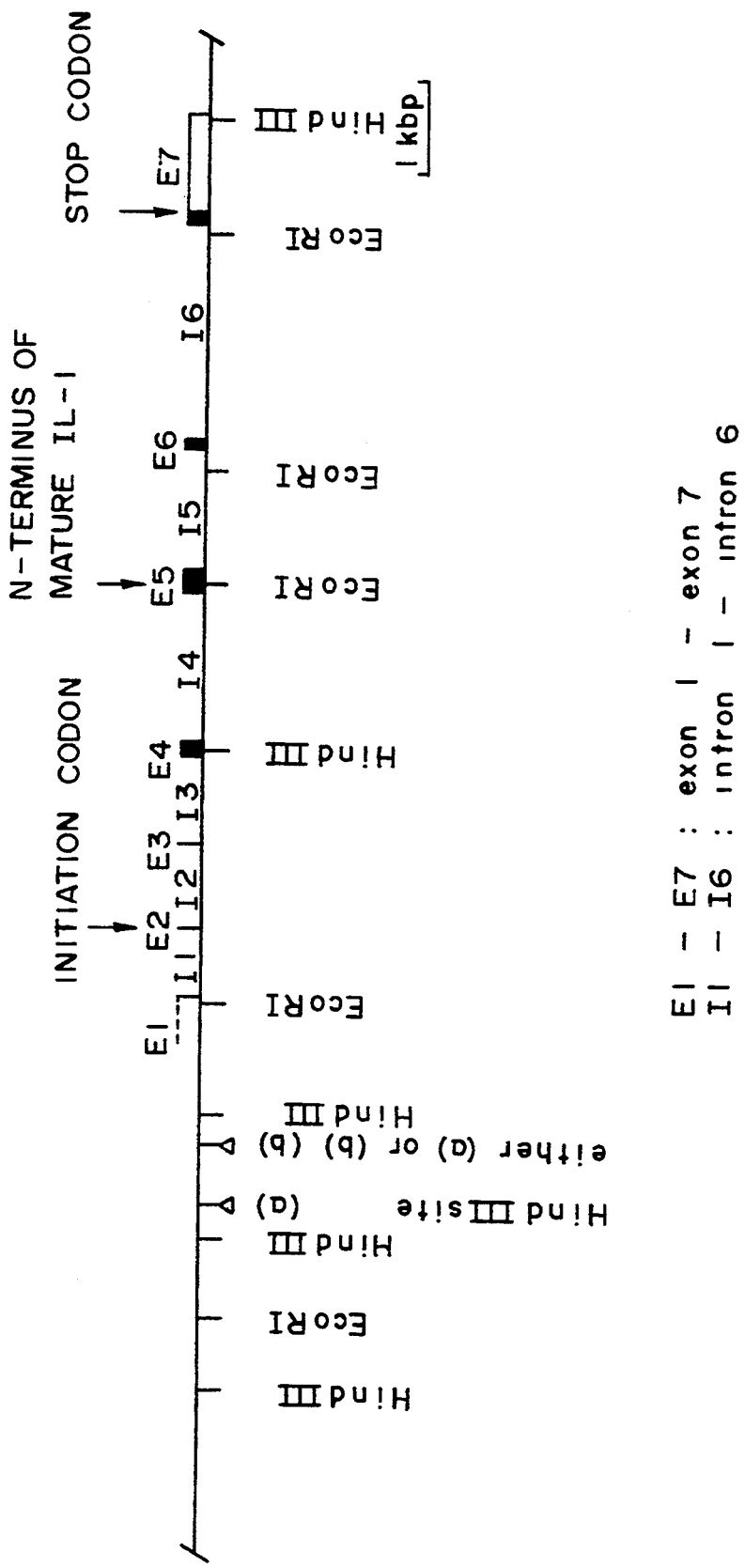
FIG. 2 shows the structure of human IL-1 chromosomal gene and its restriction endonuclease mapping (in Example 3).

FIG. 2 shows the structure of human IL-1 chromosomal gene including exons and introns. Table 6 shows the nucleotide sequence in the regions encoding human IL-1 precursor, and the amino acid sequence corresponding to human IL-1 precursor. In this table, the intron regions were shown by dotted lines.

The nucleotide sequence encoding human IL-1 obtained above agrees completely with the nucleotide sequence of the cloned cDNA encoding human IL-1 as mentioned in Example 1.

Figure 3:
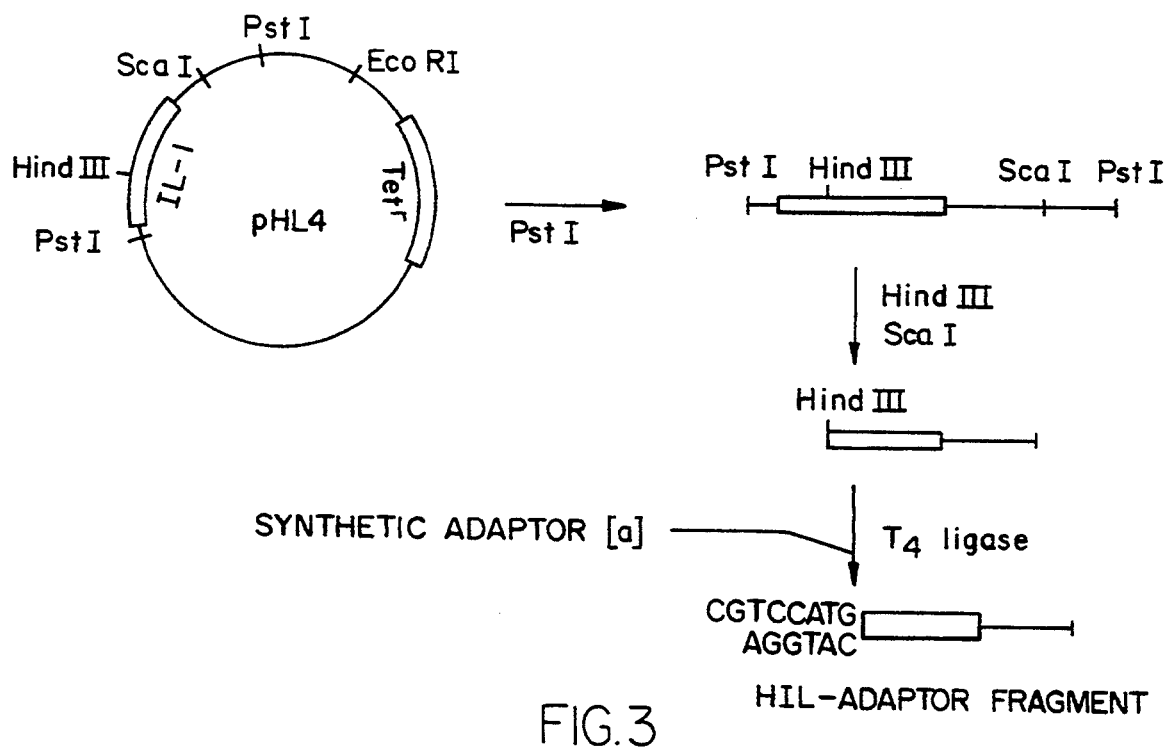
FIGS. 3-5 show the steps of construction of expression vector pHLP101 (in Example 4).
Figure 4:
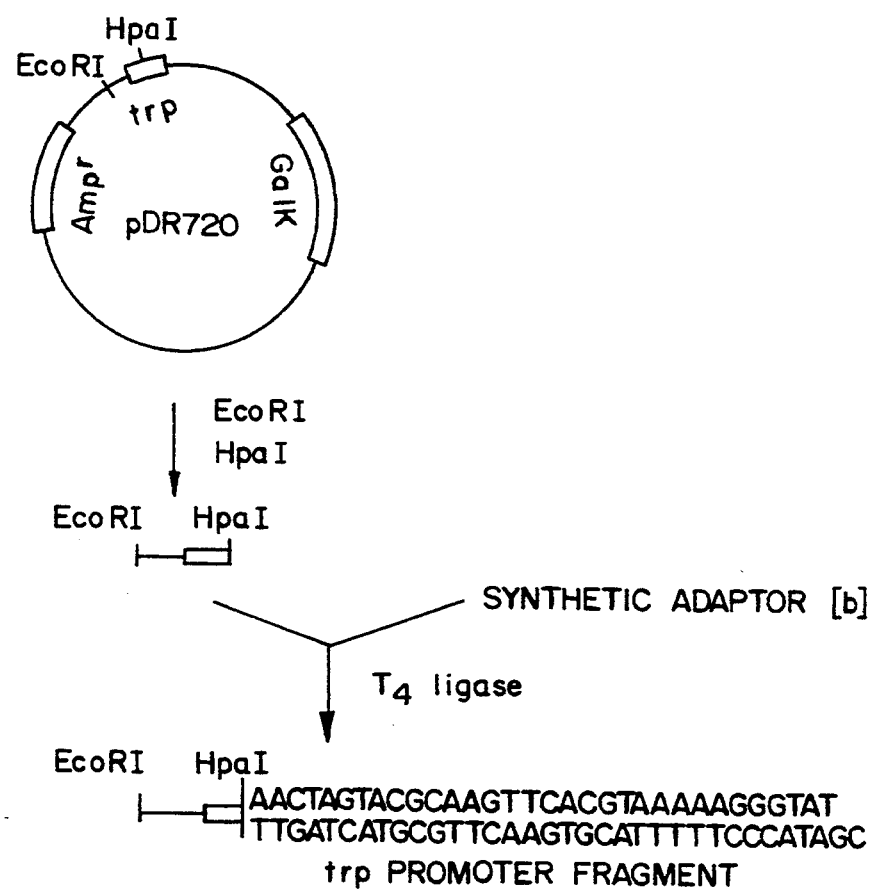
Figure 5:
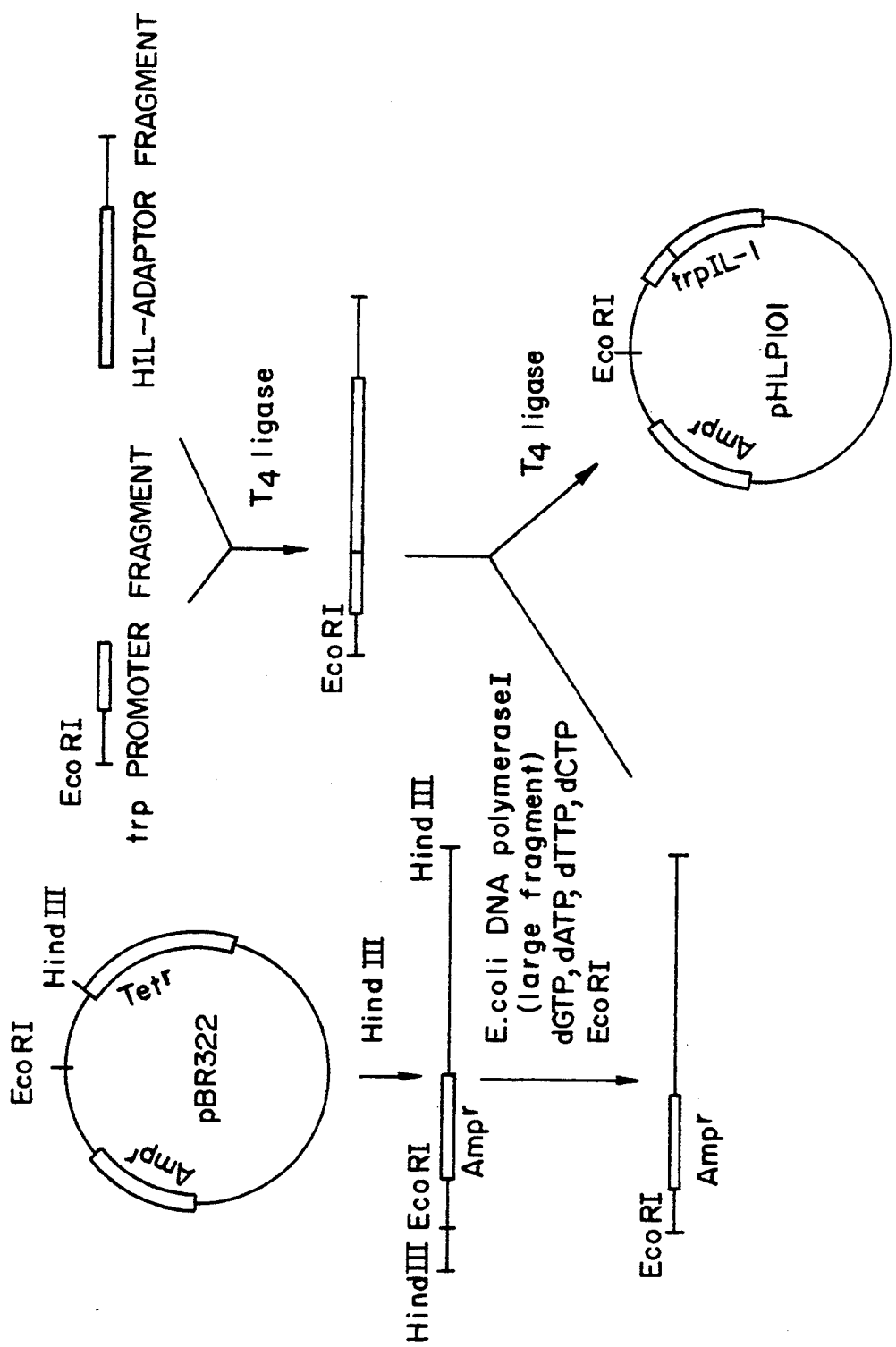

Example 4 Production of human IL-1 polypeptide (1) Construction of human IL-1 producing transformant An expression plasmid designated for producing human IL-1 was constructed by using a trp promoter as illustrated in FIG. 3–5.

The cloned cDNA encoding human IL-1 was isolated from the recombinant plasmid pHL4 as mentioned in Example 1(6). Twenty micrograms of the cDNA were dissolved in 100 microliters of 10 mM Tris-HCl (pH 7.5) buffer containing 50 mM NaCl, 6 mM MgCl$_2$ and 6 mM 2-mercaptoethanol, and it was added with 240 units of restriction endonuclease HindIII, and then incubated at 37° C. for 60 minutes. Then, 100 microliters of 0.2M NaCl and 100 units of restriction endonuclease ScaI were added, and further incubated at 37° C. for 60 minutes. At the end of incubation, NaCl was added into the reaction mixture to give a final concentration of 0.3M, and the resulting DNA fragments were recovered by precipitation with 2 volumes of ethanol. About 1.6 kbp DNA fragment containing a coding region for human IL-1 was isolated by 5% polyacrylamide gel electrophoresis, in an yield of about 5 micrograms.

This DNA fragment was ligated with a chemically synthesized oligodeoxyribonucleotide adapter by T4 ligase.

The synthetic adaptor is represented by the following formula.

[a]

The resulting DNA fragment is referred to as the HIL-adaptor fragment.

The trp promoter region was cut out from a trp promoter vector pDR720 [Russell, D. R., et al., Gene, 20, 231 (1982); product of P-L Biochemicals] by double digestion with restriction indonucleases EcoRI and HpaI, and a 35 bp DNA fragment containing the trp promoter region was isolated. A synthetic adaptor which was represented by the following formula, was ligated to the blunt-end of the 35 bp DNA fragment by using T4 ligase. The resulting DNA fragment is, hereinafter, referred to as the "trp promoter fragment".

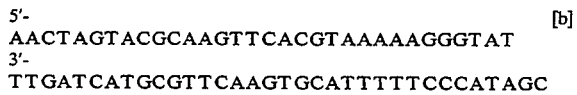

[b]

Separately, 20 micrograms of plasmid pBR322 was dissolved in 100 microliters of 10 mM Tris-HCl (pH 7.5) buffer containing 50 mM NaCl, 6 mM MgCl$_2$, 6 mM 2-mercaptoethanol and 180 units of restriction endonuclease HindIII, and incubated at 37° C. for 60 minutes. The resulting DNA was recovered by extraction with phenol/chloroform and precipitation from ethanol. And this DNA fragment was dissolved in 20 microliters of the TE solution. To ten microliters of the solution, 40 microliters of 62.5 mM Tris-HCl (pH 7.2) buffer containing 12.5 mM MgCl$_2$, 0.125 mM dithiothreitol, 0.25 mM dGTP, 0.25 mM dATP, 0.25 mM dTTP, 0.25 mM dCTP, 2.5 micrograms of bovine serum albumin and 2.6 units of E. coli DNA polymerase I (large fragment), was added, and incubated at 20° C. for 60 minutes. The resulting DNA fragment was recovered by extraction with phenol/chloroform and precipitation from ethanol. The DNA fragment was dissolved in 20 microliters of the TE solution. The above procedure gave a linealized double stranded DNA fragment which was digested with restriction endonuclease HindIII and then repaired the both ends to blunt-ends. Then, the DNA fragment was cut with restriction endonuclease EcoRI into two fragments. A larger DNA fragment (about 4.3 kbp) containing the ampicillin resistance gene was isolated (hereinafter referred to as the "pBR322-Amp$^r$ fragment").

The previously prepared HIL-adaptor fragment was ligated with the trp promoter fragment by T4 ligase at the ClaI cohesive termini of these two fragments. The resulting DNA fragment which had an EcoRI cohesive end and a blunt end, was ligated with the pBR322-Amp$^r$ fragment by T4 ligase to construct an expression plasmid (pHLP101) for production of human IL-1.

The resulting expression plasmid pHLP101 was introduced into E. coli HB101 by the following method.

E. coli HB101 was inoculated in 5 ml of the L broth and cultivated overnight at 37° C. One milliliter of the resulting culture was inoculated in 100 ml of L broth, and further cultivated at 37° C. until the turbidity at 650 nm of the culture reached 0.6. After standing for 30 minutes in ice water, the cells were collected by centrifugation and suspended in 50 ml of 50 mM CaCl$_2$, followed by standing at 0° C. for 60 minutes. The cells were then collected by centrifugation and again suspended in 10 ml of 50 mM CaCl$_2$ containing 20% glycerol.

The expression plasmid pHLP101 was mixed with the calcium treated E. coli HB101 as above, and incubated in ice water for 20 minutes, then at 42° C. for 1 minute and further at room temperature for 10 minutes, and LB broth was added. The mixture was shaken at 37° C. for 60 minutes. An aliquot of the resulting cell suspension was seeded on LB agar plates containing 25 micrograms/ml of ampicillin, and cultivated overnight at 37° C. Then, ampicillin-resistant colonies were selected to obtain transformants. One of the transformants was named HB101/pHLP101 and it was used for production of human IL-1.

(2) Production of human IL-1 polypeptide

The transformant (HB101/pHLP101) was cultivated at 37° C. overnight in the LB broth. One-tenth milliliter of the culture was inoculated in 10 ml of the modified M9 medium (composition: 1.5% Na$_2$HPO$_4$.12H$_2$, 0.3% KH$_2$PO$_4$, 0.05% NaCl, 0.1% NH$_4$Cl, 2 mg/liter vitamin B$_1$, 0.5% casamino acid, 2 mM MgSO$_4$, 0.1 mM CaCl$_2$, and 0.5% glucose) and cultivated at 37° C. for 1 hour. Then, 3-indoleacrylic acid was added to a final concentration of 20 micrograms/ml, and the cultivation was continued further for 24 hours. Then, the cells were collected by centrifugation. The cells were suspended in 1 ml of 50 mM Tris-HCl (pH8.0) buffer containing 0.1% lysozyme and 30 mM NaCl and allowed to stand at 0° C. for 30 minutes. Further, freezing on a dry ice/ethanol bath and thawing at 37° C. were repeated 6-times. And, the cell debris was removed by centrifugation to give a clarified lysate.

The IL-1 activity of the lysate was determined according to the method as mentioned in Example 1-(1).

A 16-fold diluted solution of the lysate showed $^3$H-thymidine incorporation of 8,103 cpm, which was corresponded to about 3-times or more higher incorporation than control level. It indicates that the lysate prepared as above contains human IL-1 polypeptide.

Figure 6:
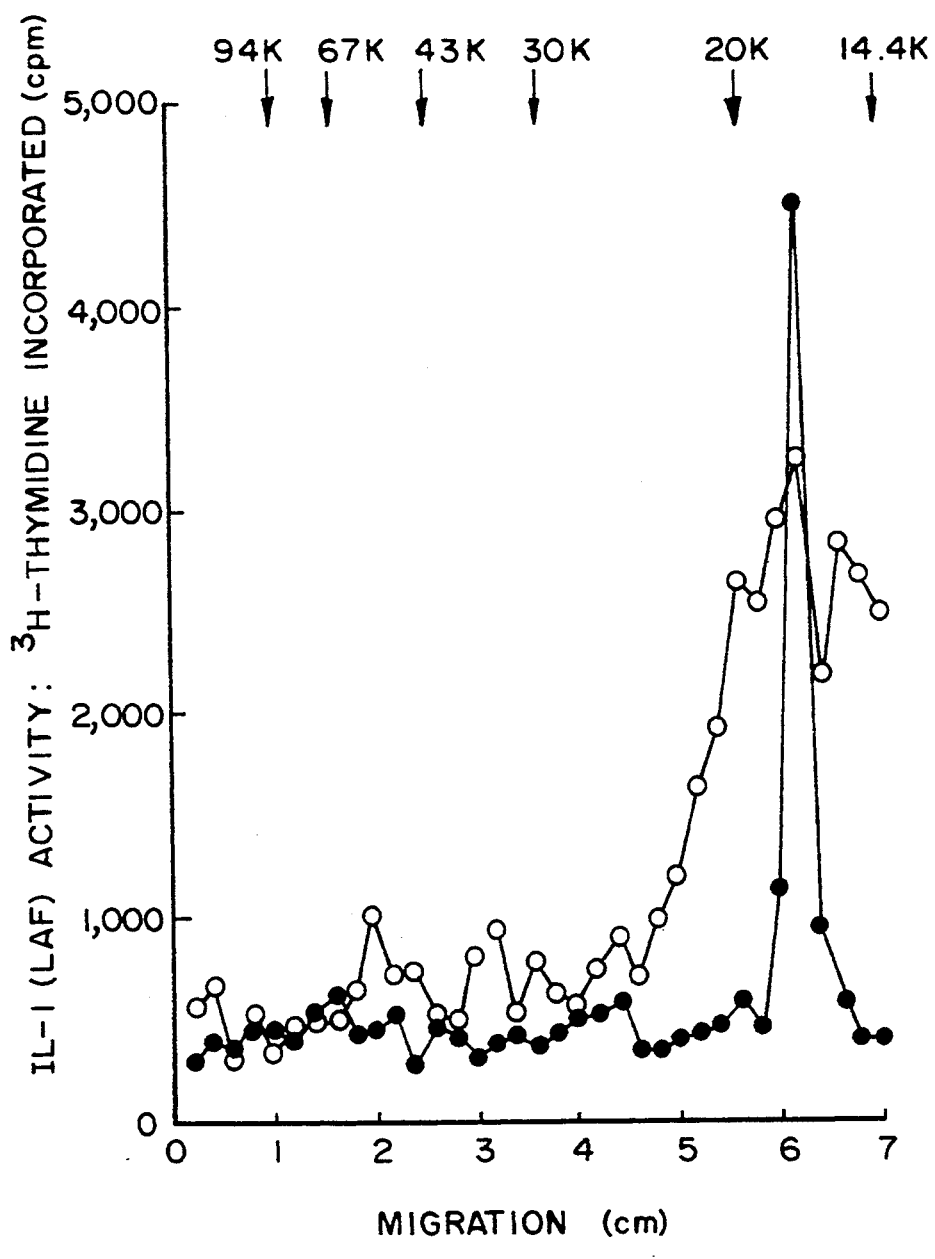
FIG. 6 shows SDS-polyacrylamide gel electrophoretic pattern of IL-1 (209) obtained in Example 4.

The SDS-polyacrylamide gel electrophoretic pattern of the lysate was shown in FIG. 6 by comparison with that of mature human IL-1 polypeptide obtained in Example 5-(2). The product produced by E. coli HB101/pHLP101 is expected to be a polypeptide consisting of 209 amino acid residues corresponding to the amino acid No. 63 to the amino acid No. 271 in Table 5. The expected molecular weight should be theoretically 23,642 if N-terminal methionine was removed. As shown in FIG. 6, however, IL-1 activity was detected in three fractions. The major peak having IL-1 activity was detected at the position corresponding to 18 kilodaltons (KD). 18 KD polypeptide might be mature human IL-1 corresponding to the region from the amino acid No. 113 to the amino acid No. 271 in Table 5.

This result indicates that the product might be gradually processed by an enzyme(s) in E. coli into polypeptides including mature human IL-1 polypeptide.

Figure 7:
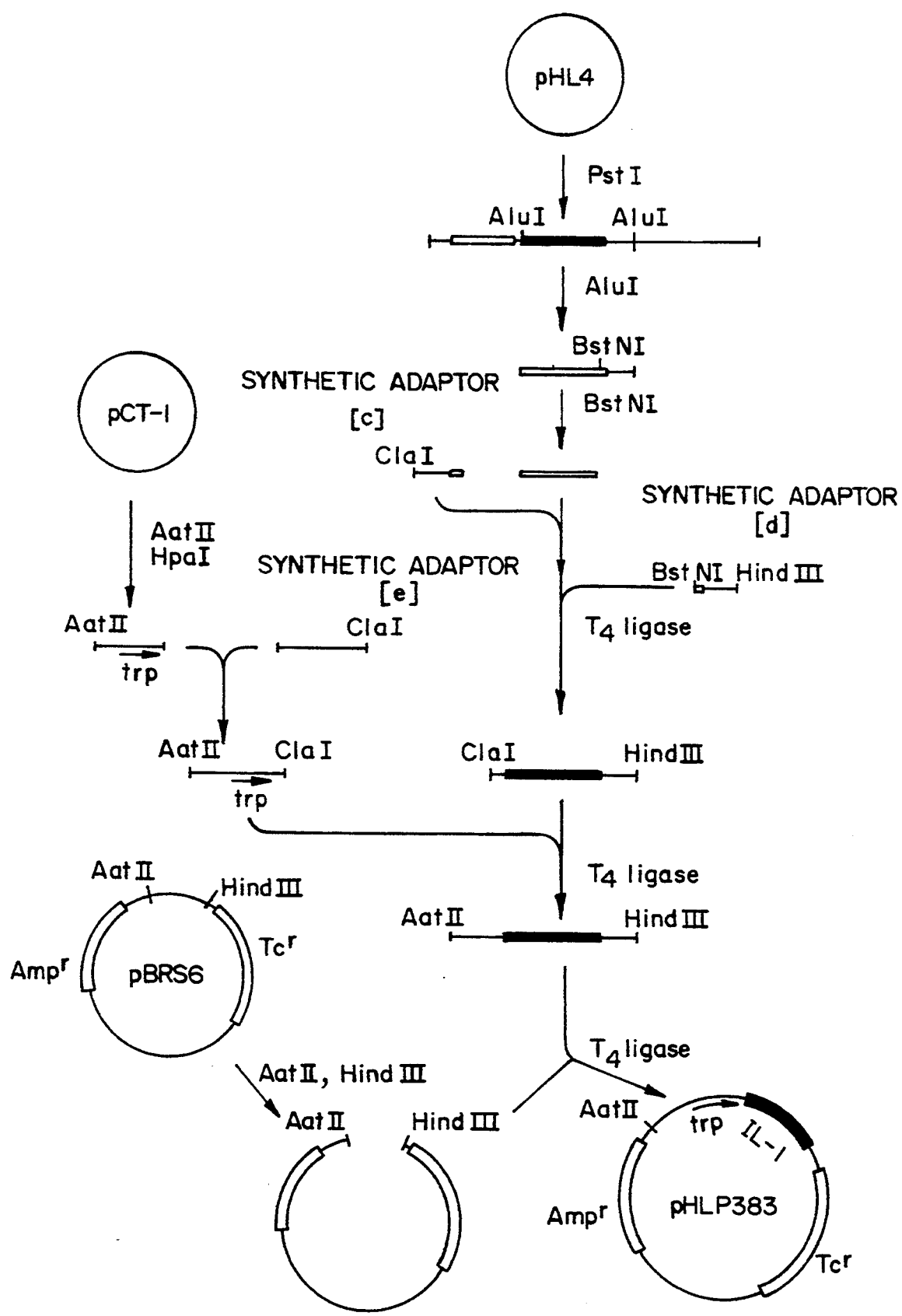
FIG. 7 shows the steps of construction of the expression vector pHLP383 (in Example 5).

Example 5 Production of mature human IL-1 polypeptide (1) Construction of mature human IL-1 producing transformant An expression plasmid (pHLP383) for producing mature human IL-1 polypeptide consisting of 159 amino acids corresponding to the amino acids from No. 113 to 271 shown in Table 5, was constructed as illustrated in FIG. 7.

The cloned cDNA encoding mature human IL-1 was isolated by digestion with restriction endonuclease PstI from the recombinant plasmid pHL4 as mentioned in Example 1-(6). The cDNA was further digested with restriction endonuclease AluI to obtain a DNA fragment being about 533 bp in size corresponding to the DNA downstream from the base No. 351 in Table 5. Furthermore, the DNA fragment was digested with restriction endonuclease BstNI to isolate the DNA fragment corresponding to the base No. 351 to 808 in Table 5. The resulting DNA fragment was sequentially ligated by T4 ligase with chemically synthesized oligodeoxyribonucleotide adaptors represented by the following formulae.

  [c]

and

  [d]

The DNA fragment having the initiation codon ATG to the 5' end of the DNA fragment encoding mature human IL-1 polypeptide consisting of 159 amino acids as mentioned above and the double stop codons TGATGA to the 3' end of it was constructed (hereinafter, referred to as "HIL-1 fragment".

About 380 bp DNA fragment containing the trp promoter region was cut out from a plasmid pCT-1 [Ikehara, M., et al., Proc. Natl. Acad. Sci. USA, 81, 5956 (1984)] by double digestion with restriction endonucleases HpaI and AatII and isolated. The DNA fragment was ligated by T4 ligase with a chemically synthesized oligodeoxyribonucleotide adaptor represented by the following formula.

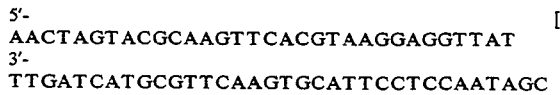  [e]

The resulting DNA fragment was ligated with the previously prepared HIL-1 fragment by T4 ligase (hereinafter referred to as the "promoter-HIL-1 fragment").

Separately, plasmid pBR322 was digested with restriction endonucleases AvaI and PvuII, and the resulting larger DNA fragment (about 3.7 kbp in size) was isolated by 0.7% agarose gel electrophoresis. After filling-in its cohesive ends to blunt-ends with E. coli DNA polymerase I (large fragment) and four kinds of deoxyribonucleotide triphosphates, both ends were ligated by T4 ligase to construct a new plasmid (designated pBRS6).

The plasmid pBRS6 was cleaved with restriction endonuclease AatII and HindIII into two fragments, and a larger DNA fragment (about 3.6 kbp) was isolated. Then, this fragment was ligated by T4 ligase with the promoter-HIL-1 fragment previously prepared in order to construct an expression plasmid pHLP383.

The resulting expression plasmid pHLP383 was introduced into E. coli HB101 by the method described in Example 4-(1). The transformant for production of mature human IL-1 was named HB101/pHLP383.

(2) Production of mature human IL-1 polypeptide

The transformant (HB101/pHLP383) was cultivated overnight in the LB broth. Ten milliliters of the culture were inoculated in 1 liter of the modified M9 medium and cultivated at 37° C. for 1 hour. Then, 3-indoleacrylic acid was added to a final concentration of 20 micrograms/ml, and the cultivation was continued further for 24 hours. Then, the cells were collected by centrifugation. The cells were suspended in 100 ml of 50 mM Tris-HCl (pH 8.0) buffer containing 0.1% lysozyme and 30 mM NaCl and allowed to stand at 0° C. for 30 minutes. Then, the suspension was freezed in a dry ice/ethanol bath and thawed at 37° C. After this freezing-thawing procedure was repeated 6-times, 2 ml of a 10% polyethyleneimine solution was added to the cell suspension and it was allowed to stand. The cell debris was removed by centrifugation to give a clarified extract.

The extract was mixed with an equal volume of saturated ammonium sulfate solution. After standing, a precipitate was collected by centrifugation. The precipitate was dissolved in about 100 ml of 20 mM Tris-HCl (pH 8.0) buffer, and dialyzed against the same buffer. The dialysate was applied onto the column of DEAE-Sepharose CL-6B which was previously equilibrated with the same buffer. The column was washed with the same buffer, and eluted with a linear gradient of NaCl from 0 to 0.5M. The fractions having IL-1 activity were collected and pooled. Then, it was concentrated by ultrafiltration and subjected to gel filtration using a Sephacryl S-200 column. The fractions having IL-1 activity were collected and pooled. The purified preparation was obtained by repeating the above procedures of DEAE-Sepharose CL-6B column chromatography and Sephacryl S-200 gel filtration.

Finally, about 15 mg of the purified human IL-1 polypeptide were obtained from the cell extract prepared from 1 liter culture.

By SDS-polyacrylamide gel electrophoretic analysis of the purified preparation, only a single protein having IL-1 activity was detected and any impurities were not detected. The chemical and physiochemical properties of the purified mature human IL-1 polypeptide were as shown in Table (a) hereinbefore.

The IL-1 activity of the purified human IL-1 polypeptide solution (approx. 40 micrograms/ml) was determined, and its results were summarized in the following table.

TABLE (d)

| dilution of sample (fold) | IL-1 activity<br>³H-thymidine incorporated (cpm) |
|---|---|
| 100,000 | 32,746 cpm |
| 1,000,000 | 14,498 |
| 10,000,000 | 4,206 |
| 100,000,000 | 2,582 |
| control | 3,210 |

The purified mature IL-1 polypeptide was soluble in phosphate buffered saline at about 1%.

(3) Antitumor effect of mature human IL-1 polypeptide

The purified mature human IL-1 polypeptide obtained above was investigated on antitumor effect on B-16 melanoma and Meth A sarcoma transplanted into mice.

The antitumor effect on mice bearing B-16 melanoma was evaluated by the following method.

C57BL/6 female mice (6 week old) were intradermally transplanted with 0.1 ml of 20% brei. On the 7th day after the tumor transplantation, mature human IL-1 polypeptide obtained in Example 5-(2) was administered into the tumor mass, intramuscularly or intravenously. Endotoxin content of the mature human IL-1 polypeptide preparation used was less than 0.08 ng per mg protein.

As a result, the growth of B-16 melanoma transplanted was significantly regressed by consecutive administration for 7 days at a dose of 3 micrograms/mouse/day into the tumor mass, showing the growth inhibition rate of 79%. And by increasing its dose upto 10-fold, the B-16. melanoma transplanted was completely regressed in 6 cut of 7 mice. In the cases of intravenous and intramuscular injection at a dose of 30 micrograms/mouse/day for 7 days from the 7th day after the tumor transplantation, the growth of B-16 melanoma transplanted was significantly suppressed at inhibition rates of 45% and 68%, respectively.

Antitumor effect on mice bearing Meth A sarcoma was evaluated by the following method.

BALB/c female mice (8 week old) were intradermally transplanted with $2 \times 10^5$ Meth A sarcoma cells. On the 7th day after the tumor transplantation, indomethacin was previously administered orally at a dose of 2 mg/kg. At 30 minutes later, mature human IL-1 polypeptide was intramuscularly injected once at a dose of 30 micrograms/mouse, and then indomethacin was administered orally twice at the same dose at 6 and 24 hours after IL-1 injection.

As a result, Meth A sarcoma transplanted was significantly inhibited to grow at the growth inhibition rates of 96% and 62% by treatment of mature human IL-1 polypeptide with and without indomethacin, respectively. The rates of complete regression was 3/7 and 2/7, respectively.

(4) Antiinfectious effect of mature human IL-1 polypeptide

Std-ddY male mice weighing about 20 g were intraperitoneally infected with $1.5 \times 10^1$ *Klebsiella pneumoniae* P-5709 cells per mouse. Mature human IL-1 polypeptide was intramuscularly (im) injected once daily at indicated doses at indicated days prior to the infection as shown in Table (e). Mortality was evaluated at 14 days after the infection.

Mature human IL-1 polypeptide showed prophylactic and therapeutic effects on the infection as shown in the following table.

TABLE (e)

Prophylactic and therapeutic effects of the experimental infection

| Medication Route* | Dose | No. of mice (Survival/Tested) | Percent Survival |
|---|---|---|---|
| im | 3 μg/mouse | 3/8 | 37.5 |
| (−3 d, −1 d) | 1 μg/mouse | 0/8 | 0 |
| | 0.3 μg/mouse | 0/8 | 0 |
| | 0.1 | 0/8 | 0 |
| im | 3 μg/mouse | 8/8 | 100 |
| (−1 d, 0 h) | 1 μg/mouse | 1/8 | 12.5 |
| | 0.3 μg/mouse | 0/8 | 0 |
| | 0.1 μg/mouse | 0/8 | 0 |
| im | 3 μg/mouse | 8/8 | 100 |
| (0 h, 24 h) | 1 μg/mouse | 5/8 | 62.5 |
| | 0.3 | 0/8 | 0 |
| | 0.1 | 0/8 | 0 |
| Control infected | | 0/8 | 0 |

[Note]: *)—3 d, −1 d, 0 h and 24 h mean the IL-1 injection at 3 days before the infection, 1 day before, immediately after, and 24 hours after, respectively.

Example 6 Production of a modified polypeptide of human IL-1 polypeptide (1) Construction of human IL-1(157) producing transformant An expression plasmid (pHLP384) for producing human IL-1 polypeptide consisting of 157 amino acids corresponding to the amino acids from No. 115 to 271 shown in Table 5, which was referred to as IL-1(157) polypeptide, was constructed according to the essentially same method as mentioned in Example 5-(1), except for using a chemically synthesized oligodeoxyribonucleotide adaptor as shown below instead of the synthetic adaptor [c].

```
5'-CGATTATGCCTTTTAG        [f]
3'-TAATACGGAAAATC
```

The resulting expression plasmid pHLP384 was introduced into *E. coli* HB101 by the method described in Example 4-(1). The transformant for production of human IL-1(157) polypeptide was named HB101/pHLP384.

(2) Production of human IL-1(157) polypeptide

The transformant (HB101/pHLP384) was cultivated overnight in the LB broth. Ten milliliters of the culture were inoculated in 1 liter of the modified M9 medium and cultivated at 37° C. for 1 hour. Then, 3-indoleacrylic acid was added to a final concentration of 20 micrograms/ml, and the cultivation was continued further for 24 hours. Then, the cells were collected by centrifugation. The cells were suspended in 100 ml of 50 mM Tris-HCl (pH 8.0) buffer containing 0.1% lysozyme and 30 mM NaCl and allowed to stand at 0° C. for 30 minutes. Then, the suspension was freezed in a dry ice/ethanol bath and thawed at 37° C. After this freezing-thawing procedure was repeated 6-times, 2 ml of 10% polyethyleneimine solution was added to the cell suspension and it was allowed to stand. The cell debris was removed by centrifugation to give a clarified extract.

The extract was mixed with an equal volume of saturated ammonium sulfate solution. After standing, a precipitate was collected by centrifugation. The precipitate was dissolved in about 100 ml of 20 mM Tris-HCl (pH 8.0) buffer, and dialyzed against the same buffer. The dialysate was applied onto the column of DEAE-Sepharose CL-6B which was previously equilibrated with the same buffer. The column was washed with the same buffer, and eluted with a linear gradient of NaCl from 0 to 0.5M. The fractions having IL-1 activity were collected and pooled. Then, it was concentrated by ultrafiltration and subjected to gel filtration by using a Sephacryl S-200 column. The fractions having IL-1 activity were collected and pooled.

The resulting solution had IL-1 activity, showing $^3$H-thymidine incorporation of 45,394 cpm when $1\times10^4$-fold sample dilution was assayed.

Chemical and physicochemical properties of the human IL-1(157) polypeptide are as shown in Table (b) hereinbefore.

Figure 8:
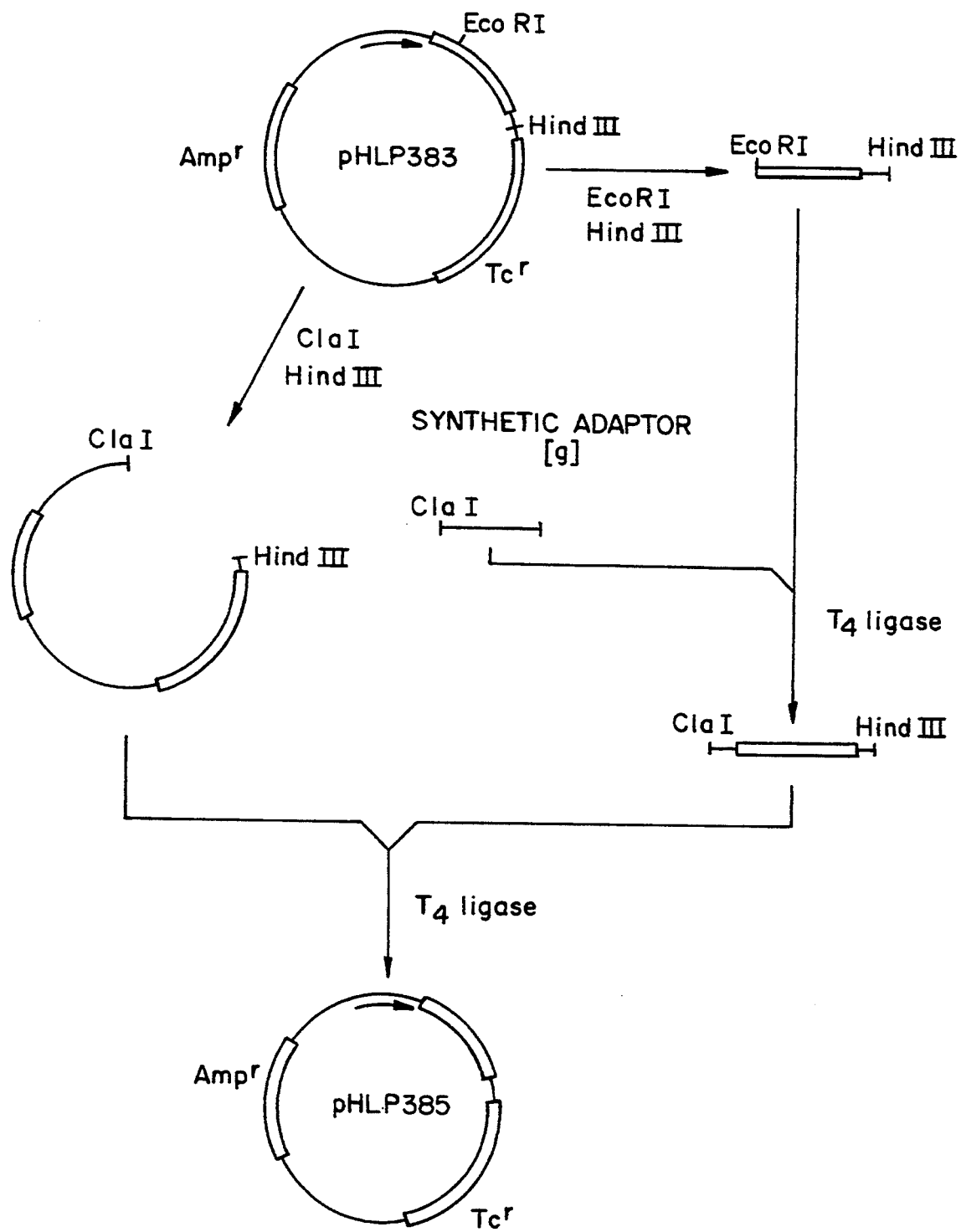
FIG. 8 shows the steps of construction of the expression vector pHLP385 (in Example 7).

Example 7 Production of a modified polypeptide of human IL-1 polypeptide (1) Construction of human IL-1 (149) producing transformant An expression plasmid (pHLP385) for producing human IL-1 polypeptide consisting of 149 amino acids corresponding to the amino acids from No. 123 to 271 shown in Table 5, which was referred to as IL-1(149) polypeptide, was constructed as illustrated in FIG. 8.

The recombinant plasmid pHLP383 obtained in Example 5-(1) was digested with restriction endonucleases EcoRI and HindIII to isolate about 422 bp DNA fragment corresponding to the nucleotide sequence of the downstream region from the base No. 398 in Table 5. The resulting DNA fragment was ligated by T4 ligase with a chemically synthesized oligodeoxyribonucleotide adaptor represented by the following formula.

5'-CGATTATGAAATACAACTTTATGAGGATCATCAAATACG  [g]
3'-TAATACTTTATGTTGAAATACTCCTAGTAGTTTATGCTTAA

Separately, the recombinant plasmid pHLP383 was cleaved with restriction endonucleases ClaI and HindIII, and the resulting larger DNA fragment containing a part of trp promoter region, an ampicillin resistance gene and a tetracycline resistance gene was isolated.

To this DNA fragment, the previously prepared DNA fragment was ligated by T4 ligase in order to construct an expression plasmid pHLP385 for production of the above polypeptide consisting of 149 amino acids.

The resulting expression plasmid pHLP385 was introduced into E. coli HB101 by the method described in Example 4-(1). The transformant for production of human IL-1(149) polypeptide was named HB101/pHLP385.

(2) Production of human IL-1(149) polypeptide

According to the method as mentioned in Example 6-(2), the transformant (HB101/pHLP385) was cultivated, and then the desired polypeptide was isolated from the cell extract.

The obtained polypeptide had IL-1 activity, showing $^3$H-thymidine incorporation of 27,766 cpm when $1\times10^4$-fold sample dilution was assayed.

Chemical and physicochemical properties are as shown in Table (b) hereinbefore.

Example 8 Production of a modified polypeptide of human IL-1 polypeptide (1) Construction of human IL-1(144) producing transformant An expression plasmid (pHLP386) for producing human IL-1 polypeptide consisting of amino acids corresponding to the amino acids from No. 127 or 128 to 271 shown in Table 5, which was referred to as IL-1(144) polypeptide, was constructed according to the method as mentioned in Example 7-(1), except for using a chemically synthesized oligodeoxyribonucleotide adaptor as shown below instead of the synthetic adaptor [g].

5'-CGATTATGAGGATCATCAAATACG  [h]
3'-TAATACTCCTAGTAGTTTATGCTTAA

The resulting expression plasmid pHLP386 was introduced into E. coli HB101 by the method described in Example 4-(1). The transformant for production of human IL-1(144) polypeptide was named HB101/pHLP386.

(2) Production of human IL-1(144) polypeptide

According to the method as mentioned in Example 6-(2), the transformant (HB101/pHLP386) was cultivated, and then the desired polypeptide was isolated from the cell extract.

The obtained polypeptide had IL-1 activity, showing $^3$H-thymidine incorporation of 15,092 cpm when $1\times10^3$-fold sample dilution was assayed.

Chemical and physicochemical properties of human IL-1 polypeptide are as shown in Table (b) hereinbefore.

Example 9 Production of a modified polypeptide of human IL-1 polypeptide (1) Construction of human IL-1(143) producing transformant An expression plasmid (pHLP387) for producing human IL-1 polypeptide consisting of 143 amino acids corresponding to the amino acids from No. 129 to 271 shown in Table 5 which was referred to as IL-1(143) polypeptide, was constructed according to the method as mentioned in Example 7-(1), except for using a chemically synthesized oligodeoxyribonucleotide adaptor as shown below instead of the synthetic adaptor [g].

5'-CGATTATGATCATCAAATACG  [i]
3'-TAATACTAGTAGTTTATGCTTAA

The resulting expression plasmid pHLP387 was introduced into E. coli HB101 by the method described in Example 4-(1). The transformant for production of human IL-1(143) polypeptide was named HB101/pHLP387.

(2) Production of human IL-1(143) polypeptide

According to the method as mentioned in Example 6-(2), the transformant (HB101/pHLP387) was cultivated, and then the desired polypeptide was isolated from the cell extract.

The obtained polypeptide had IL-1 activity, showing $^3$H-thymidine incorporation of 12,700 cpm when 10-fold sample dilution was assayed.

Figure 9:
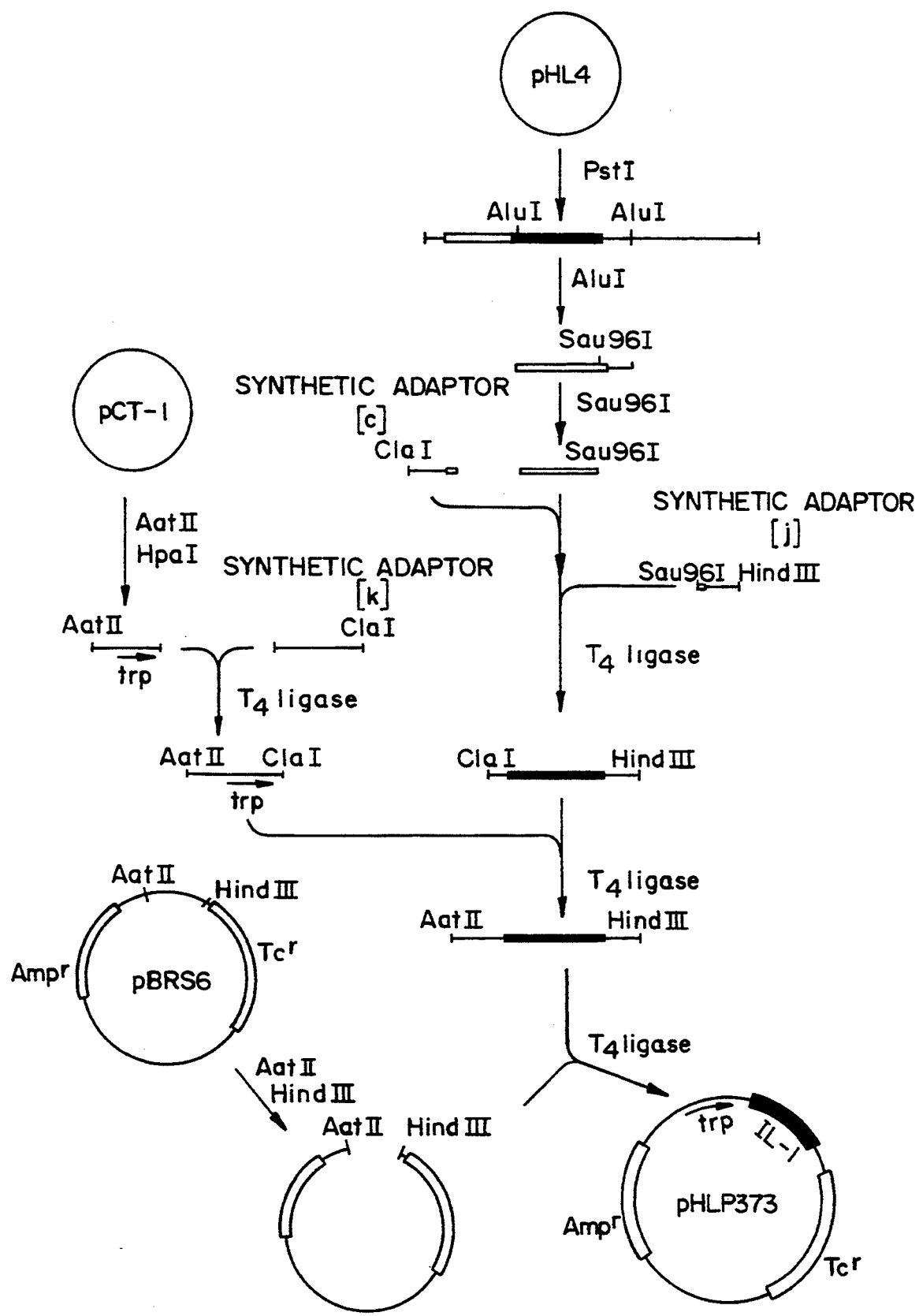
FIG. 9 shows the steps of construction of the expression vector pHLP373 (in Example 10.

Example 10 Production of a modified polypeptide of human IL-1 polypeptide (1) Construction of human IL-1(155-C) producing transformant An expression plasmid (pHLP373) for producing human IL-1 polypeptide consisting of 155 amino acids corresponding to the amino acids from No. 113 to 267 shown in Table 5, was constructed as illustrated in FIG. 9.

The cloned cDNA encoding human IL-1 was isolated by digestion with restriction endonuclease PstI from the recombinant plasmid pHL4 as mentioned in Example 1-(6). The cDNA was further digested with restriction endonuclease AluI to obtain a DNA fragment being about 533 bp in size corresponding to the DNA downstream from the base No. 351 in Table 5. Furthermore, the DNA fragment was digested with restriction endonuclease Sau96I to isolate the DNA fragment corresponding to the base No. 351 to 769 in Table 5. The resulting DNA fragment was sequentially ligated by T4 ligase with chemically synthesized oligodeoxyribonucleotide adaptors represented by the following formulae.

5'-CGATTATGTCATCACCTTTTAG      [c]
3'-TAATACAGTAGTGGAAAATC and

5'-GGCCACCCTCTATCACTGACTTTCAGATACTGTGATGA     [j]
3'-GTGGGAGATAGTGACTGAAAGTCTATGACACTACTTCGA

The DNA fragmant having the initiation codon ATG at the 5' end of the DNA fragment encoding human IL-1 polypeptide consisting of 155 amino acids as mentioned above and the double stop codons TGATGA at the 3' end of it was constructed (hereinafter referred to as "HIL-155 fragment").

About 380 bp DNA fragment containing the trp promoter region was cut out from a plasmid pCT-1 by double digestion with restriction endonucleases HpaI and AatII and was isolated. The DNA fragment was ligated by T4 ligase with a chemically synthesized oligodeoxyribonucleotide adaptor represented by the following formula.

5'-AACTAGTACGCAAGTTCACGTAAGGAGGTTAT     [k]
3'-TTGATCATGCGTTCAAGTGCATTCCTCCAATAGC

The resulting DNA fragment was ligated with the previously prepared the HIL-155 fragment by T4 ligase (hereinafter referred to as the "promoter-HIL-155 fragment").

Separately, plasmid pBR322 was digested with restriction endonucleases AvaI and PvuII, and the resulting larger DNA fragment (about 3.7 kbp in size) was isolated by 0.7% agarose gel electrophoresis. After filling-in its cohesive ends to blunt-ends with E. coli DNA polymerase I (large fragment) and four kinds of deoxyribonucleotide triphosphates, both ends were ligated by T4 ligase to construct a plasmid (designated pBRS6).

The plasmid pBRS6 was cleaved with restriction endonucleases AatII and HindIII into two fragments, and a larger DNA fragment (about 3.6 kbp) was isolated. Then, this fragment was ligated by T4 ligase with the promoter-HIL-155 fragment previously prepared in order to construct an expression plasmid pHLP373.

The resulting expression plasmid pHLP373 was introduced into E. coli HB101 by the method described in Example 4-(1). The transformant for production of human IL-1(155-C) polypeptide was named HB101/pHLP373.

(2) Production of human IL-1(155-C) polypeptide

The transformant (HB101/pHLP373) was cultivated overnight in the LB broth. Ten milliliters of the culture were inoculated in 1 liter of the modified M9 medium and cultivated at 37° C. for 1 hour. Then, 3-indoleacrylic acid was added to a final concentration of 20 micrograms/ml, and the cultivation was continued further for 24 hours. Then, the cells were collected by centrifugation. The cells were suspended in 100 ml of 50 mM Tris-HCl (pH 8.0) buffer containing 0.1% lysozyme and 30 mM NaCl and allowed to stand at 0° C. for 30 minutes. Further, freezing on a dry ice/ethanol bath and thawing at 37° C. were repeated 6-times. And, the cell debris was removed by centrifugation to give a clarified extract.

The cell extract had IL-1 activity, showing $^3$H-thymidine incorporation of 27,109 cpm when $1 \times 10^5$-fold sample dilution was assayed.

Chemical and physicochemical properties of human IL-1(155-C) polypeptide are shown in Table (c) hereinbefore.

Example 11 Production of a modified polypeptide of human IL-1 polypeptide (1) Construction of human IL-1(152-C) producing transformant and production thereof An expression plasmid (pHLP358) for producing human IL-1 polypeptide consisting of 152 amino acids corresponding to the amino acids from No. 113 to 264 shown in Table 5, which was referred to as IL-1(152-C) polypeptide, was constructed according to the method as mentioned in Example 10-(1), except for using a chemically synthesized oligodeoxyribonucleotide adaptor as shown below instead of the synthetic adaptor [j].

5'-GGCCACCCTCTATCACTGACTTATGATGA     [l]
3'-GTGGGAGATAGTGACTGAATACTACTTCGA

The resulting recombinant plasmid pHLP358 was introduced into E. coli HB101 by the method described in Example 4-(1). The transformant for production of human IL-1(152-C) polypeptide was named HB101/pHLP358.

According to the method as mentioned in Example 6-(2), the transformant (HB101/pHLP358) was cultivated, and then the desired polypeptide was isolated from the cell extract.

Example 12 Production of a modified polypeptide of human IL-1 polypeptide (1) Construction of human IL-1(154-C) producing transformant An expression plasmid (pHLP363) for producing human IL-1 polypeptide consisting of 154 amino acids corresponding to the amino acids from No. 113 to 266 shown in Table 5, which was referred to as IL-1(154-C) polypeptide, was constructed according to the method as mentioned in Example 10-(1), except for using a chemically synthesized oligodeoxyribonucleotide adaptor as shown below instead of the synthetic adaptor [j]

```
5'-GGCCACCCT CT AT CACT GACT T T CAGAT AT GAT GA         [m]
    3'-GT GGGAGAT AGT GACT GAAAGT CT AT ACT ACTTCGA
```

The resulting expression plasmid pHLP363 was introduced into E. coli HB101 by the method described in Example 4-(1). The transformant for production of human IL-1(154-C) polypeptide was named HB101/pHLP363.

(2) Production of human IL-1(154-C) polypeptide

According to the method as mentioned in Example 6-(2), the transformant (HB101/pHLP363) was cultivated, and then the desired polypeptide was isolated from the cell extract.

The cell lysate had IL-1 activity, showing $^3$H-thymidine incorporation of 11,058 cpm when $1 \times 10^2$-fold sample dilution was assayed. Molecular weight of the obtained polypeptide having IL-1 activity was estimated about 17,500 daltons by SDS-polyacrylamide gel electrophoresis.

Example 13 Production of a modified polypeptide of human IL-1 polypeptide (1) Construction of human IL-1(153-C) producing transformant An expression plasmid (pHLP353) for producing human IL-1 polypeptide consisting of 153 amino acids corresponding to the amino acids from No. 113 to 265 shown in Table 5, which was referred to as IL-1(153-C) polypeptide, was constructed according to the method as mentioned in Example 10-(1), except for using a chemically synthesized oligodeoxyribonucleotide adaptor as shown below instead of the synthetic adaptor [j].

```
5'-GGCCACCCT CT AT CACT GACT T T CAGT GAT GA         [n]
    3'-GT GGGAGAT AGT GACT GAAAGT CACT ACTTCGA
```

The resulting expression plasmid pHLP353 was introduced into E. coli HB101 by the method described in Example 4-(1). The transformant for production of human IL-1(153-C) polypeptide was nambed HB101/pHLP353.

(2) Production of human IL-1(153-C) polypeptide

According to the method as mentioned in Example 6-(2), the transformant (HB101/pHLP353) was cultivated, and then the desired polypeptide was isolated from the cell extract.

The cell lysate had IL-1 activity, showing $^3$H-thymidine incorporation of 3,875 cpm when 10-fold sample dilution was assayed. Molecular weight of the obtained polypeptide having IL-1 activity was estimated about 17,500 daltons by SDS-polyacrylamide gel electrophoresis.

Example 14 Production of a modified polypeptide of human IL-1 polypeptide (1) Construction of human IL-1(140-NC) producing transformant An expression plasmid (pHLP376) for producing human IL-1 polypeptide consisting of 140 amino acids corresponding to the amino acids from No. 128 to 267 shown in Table 5, was constructed.

An expression plasmid pHLP386 obtained in Example 8 was digested with restriction endonuclease EcoRI and HindIII, and a resulting larger DNA fragment was isolated. Separately, an expression plasmid pHLP373 obtained in Example 10-(1) was digested with restriction endonucleases EcoRI and HindIII, and a resulting smaller DNA fragment was isolated. Then, the both DNA fragment as above were ligated by T4 ligase in order to construct an expression plasmid for producing the above polypeptide consisting of 140 amino acids (designated pHLP376).

The resulting recombinant plasmid pHLP376 was introduced into E. coli HB101 by the method described in Example 4-(1). The transformant for production of human IL-1(140-NC) was named HB101/pHLP376.

(2) Production of human IL-1(140-NC) polypeptide

The transformant (HB101/pHLP376) was cultivated overnight in the LB broth. Ten milliliters of the culture were inoculated in 1 liter of the modified M9 medium and cultivated at 37° C. for 1 hour. Then, 3-indoleacrylic acid was added to a final concentration of 20 micrograms/ml, and the cultivation was continued further for 24 hours. Then, the cells were collected by centrifugation. The cells were suspended in 100 ml of 50 mM Tris-HCl (pH 8.0) buffer containing 0.1% lysozyme and 30 mM NaCl and allowed to stand at 0° C. for 30 minutes. Further, freezing on a dry ice/ethanol bath and thawing at 37° C. were repeated 6-times. And, the cell debris was removed by centrifugation to give a clarified extract.

The cell extract had IL-1 activity, showing $^3$H-thymidine incorporation of 12,493 cpm when $1 \times 10^2$-fold sample dilution was assayed. Molecular weight of the obtained polypeptide having IL-1 activity was estimated about 16,000 daltons by SDS-polyacrylamide gel electrophoresis.

Example 15 Production of mature rabbit IL-1 polypeptide

Figure 10:
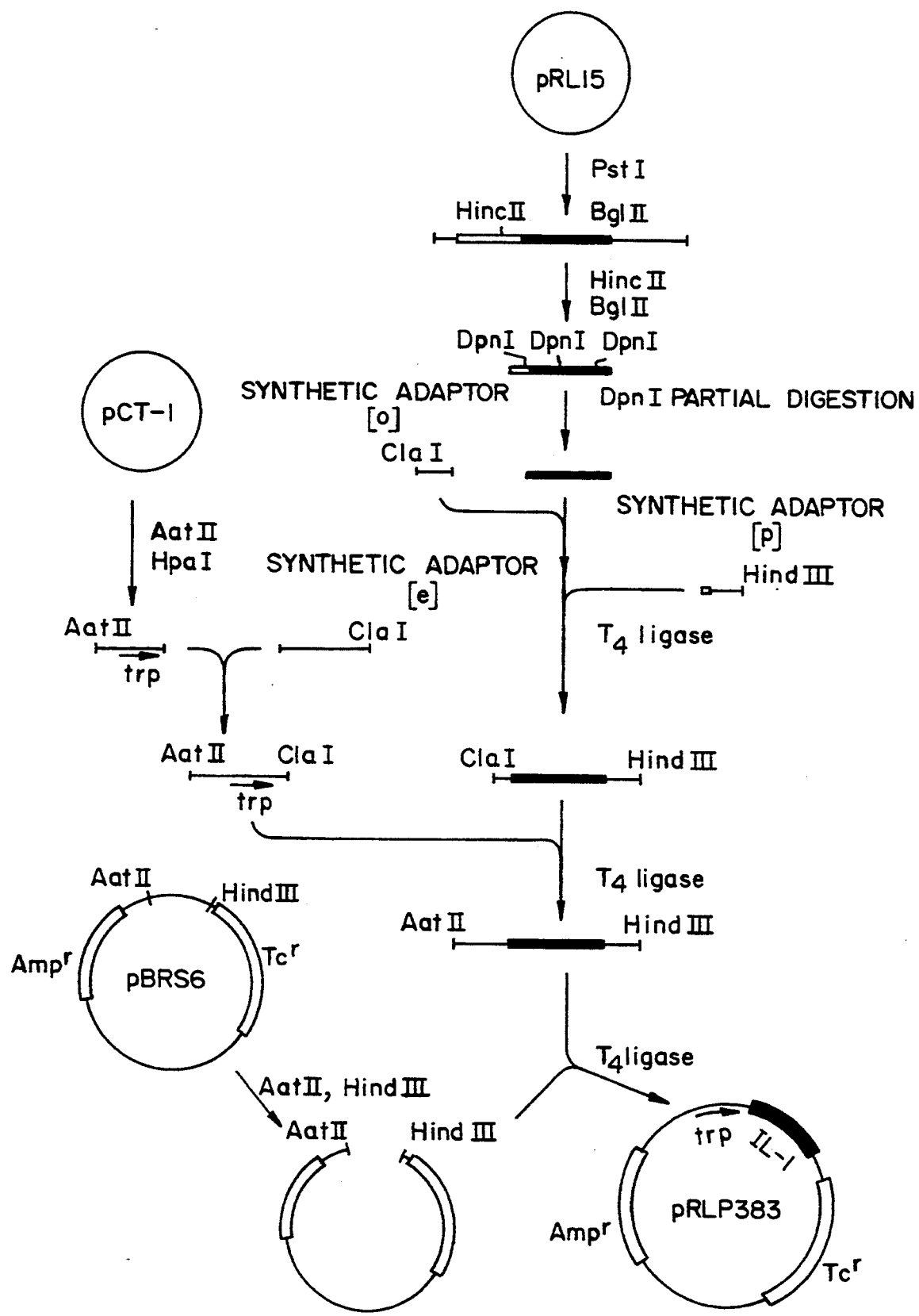
FIG. 10 shows the steps of construction of the expression vector pRLP383 (in Example 15).

An expression plasmid for producing mature rabbit IL-1 was constructed by using a trp promoter as illustrated in FIG. 10.

The cloned cDNA insert containing a coding region for mature rabbit IL-1 was isolated from the recombinant plasmid pRL15 obtained in Example 2-(6) by digestion with restriction endonuclease PstI. The cDNA was further digested with restriction endonucleases HincII and BglII to isolate a DNA fragment (about 509 bp in size). Then, the 509bp-DNA fragment was partially digested with restriction endonuclease DpnI and the resulting DNA containing most of the coding region for mature rabbit IL-1 was isolated by 5% polyacrylamide gel electrophoresis.

This DNA fragment was ligated with chemically synthesized oligodeoxyribonucleotide adaptors by T4 ligase.

The synthetic adaptors are represented by the following formulae.

5'-CGATTATG  [o]
3'-TAATAC and

5'-GATCTCATGATGA  [p]
3'-AGTACTACTTCGA

The resulting DNA fragment is referred to as the RIL-adaptor fragment.

Separately, about 380 bp DNA fragment containing the trp promoter region was cut out from a plasmid pCT-1 by double digestion with restriction endonucleases HpaI and AatII, and it was isolated. The DNA fragment was ligated by T4 ligase with a chemically synthesized oligodeoxyribonucleotide adaptor represented by the following formula.

5'-AACTAGTACGCAAGTTCACGTAAGGAGGTTAT  [e]
3'-TTGATCATGCGTTCAAGTGCATTCCTCCAATAGC

The resulting DNA fragment was sequentially ligated with the previously prepared the RIL-1-adaptor fragment and the AatII-HindIII 3.6 bp DNA fragment of plasmid pBRS6 obtained in Example 5-(1) by T4 ligase, in order to construct an expression plasmid pRLP383.

By introducing the expression plasmid pRLP383 into E. coli HB101 in accordance with the method described in Example 4-(1) and cultivating the transformant, mature rabbit IL-1 polypeptide consisting of 155 amino acids corresponding to the amino acids from No. 113 to 267 shown in Table 7 will be able to be obtained.

TABLE 1-1

| Ser | Ser | Pro | Phe | Ser | Phe | Leu | Ser | Asn | Val | Lys | Tyr | Asn | Phe | Met |
|-----|-----|-----|-----|-----|-----|-----|-----|-----|-----|-----|-----|-----|-----|-----|
| Arg | Ile | Ile | Lys | Tyr | Glu | Phe | Ile | Leu | Asn | Asp | Ala | Leu | Asn | Gln |
| Ser | Ile | Ile | Arg | Ala | Asn | Asp | Gln | Tyr | Leu | Thr | Ala | Ala | Ala | Leu |
| His | Asn | Leu | Asp | Glu | Ala | Val | Lys | Phe | Asp | Met | Gly | Ala | Tyr | Lys |
| Ser | Ser | Lys | Asp | Asp | Ala | Lys | Ile | Thr | Val | Ile | Leu | Arg | Ile | Ser |
| Lys | Thr | Gln | Leu | Tyr | Val | Thr | Ala | Gln | Asp | Glu | Asp | Gln | Pro | Val |
| Leu | Leu | Lys | Glu | Met | Pro | Glu | Ile | Pro | Lys | Thr | Ile | Thr | Gly | Ser |
| Glu | Thr | Asn | Leu | Leu | Phe | Phe | Trp | Glu | Thr | His | Gly | Thr | Lys | Asn |
| Tyr | Phe | Thr | Ser | Val | Ala | His | Pro | Asn | Leu | Phe | Ile | Ala | Thr | Lys |
| Gln | Asp | Tyr | Trp | Val | Cys | Leu | Ala | Gly | Gly | Pro | Pro | Ser | Ile | Thr |
| Asp | Phe | Gln | Ile | Leu | Glu | Asn | Gln | Ala | | | | | | |

[I-1]

TABLE 1-2

| (5')TCA | TCA | CCT | TTT | AGC | TTC | CTG | AGC | AAT | GTG | AAA | TAC | AAC | TTT |
|---------|-----|-----|-----|-----|-----|-----|-----|-----|-----|-----|-----|-----|-----|
| ATG | AGG | ATC | ATC | AAA | TAC | GAA | TTC | ATC | CTG | AAT | GAC | GCC | CTC |
| AAT | CAA | AGT | ATA | ATT | CGA | GCC | AAT | GAT | CAG | TAC | CTC | ACG | GCT |
| GCT | GCA | TTA | CAT | AAT | CTG | GAT | GAA | GCA | GTG | AAA | TTT | GAC | ATG |
| GGT | GCT | TAT | AAG | TCA | TCA | AAG | GAT | GCT | AAA | ATT | ACC | GTG | |
| ATT | CTA | AGA | ATC | TCA | AAA | ACG | CAA | TTG | TAT | GTG | ACG | GCC | CAA |
| GAT | GAA | GAC | CAA | CCA | GTG | CTG | CTG | AAG | GAG | ATG | CCT | GAG | ATA |
| CCC | AAA | ACC | ATC | ACA | GGT | AGT | GAG | ACC | AAC | CTC | CTC | TTC | TTC |
| TGG | GAA | ACG | CAC | GGC | ACG | AAG | AAC | TAT | TTC | ACA | TCA | GTT | GCC |
| CAT | CCA | AAC | TTG | TTT | ATT | GCC | ACA | AAG | CAA | GAC | TAC | TGG | GTG |
| TGC | TTG | GCA | GGG | GGG | CCA | CCC | TCT | ATC | ACG | GAC | TTT | CAG | ATA |
| CTG | GAA | AAC | CAG | GCG(3') | | | | | | | | | |

[II-1]

TABLE 2-1

| Met | Ala | Lys | Val | Pro | Asp | Met | Phe | Glu | Asp | leu | Lys | Asn | Cys | Tyr |
|-----|-----|-----|-----|-----|-----|-----|-----|-----|-----|-----|-----|-----|-----|-----|
| Ser | Glu | Asn | Glu | Glu | Asp | Ser | Ser | Ser | Ile | Asp | His | Leu | Ser | Leu |
| Asn | Gln | Lys | Ser | Phe | Tyr | His | Val | Ser | Tyr | Gly | Pro | Leu | His | Glu |
| Gly | Cys | Met | Asp | Gln | Ser | Val | Ser | Leu | Ser | Ile | Ser | Glu | Thr | Ser |
| Lys | Thr | Ser | Lys | Leu | Thr | Phe | Lys | Glu | Ser | Met | Val | Val | Val | Ala |
| Thr | Asn | Gly | Lys | Val | Leu | Lys | Lys | Arg | Arg | Leu | Ser | Leu | Ser | Gln |
| Ser | Ile | Thr | Asp | Asp | Asp | Leu | Glu | Ala | Ile | Ala | Asn | Asp | Ser | Glu |
| Glu | Glu | Ile | Ile | Lys | Pro | Arg | | | | | | | | |

[I-2]

TABLE 2-2

| (5')ATG | GCC | AAA | GTT | CCA | GAC | ATG | TTT | GAA | GAC | CTG | AAG | AAC | TGT |
|---------|-----|-----|-----|-----|-----|-----|-----|-----|-----|-----|-----|-----|-----|
| TAC | AGT | GAA | AAT | GAA | GAA | GAC | AGT | TCC | TCC | ATT | GAT | CAT | CTG |
| TCT | CTG | AAT | CAG | AAA | TCC | TTC | TAT | CAT | GTA | AGC | TAT | GGC | CCA |
| CTC | CAT | GAA | GGC | TGC | ATG | GAT | CAA | TCT | GTG | TCT | CTG | AGT | ATC |
| TCT | GAA | ACC | TCT | AAA | ACA | TCC | AAG | CTT | ACC | TTC | AAG | GAG | AGC |
| ATG | GTG | GTA | GTA | GCA | ACC | AAC | GGG | AAG | GTT | CTG | AAG | AAG | AGA |
| CGG | TTG | AGT | TTA | AGC | CAA | TCC | ATC | ACG | GAT | GAT | GAC | CTG | GAG |
| GCC | ATC | GCC | AAT | GAC | TCA | GAG | GAA | GAA | ATC | ATC | AAG | CCT | AGG(3') |

TABLE 3-1

| | | | | | | | | | | | | | |
|---|---|---|---|---|---|---|---|---|---|---|---|---|---|
| Ser | Val | Pro | Tyr | Thr | Phe | Gln | Arg | Asn | Met | Arg | Tyr | Lys | Tyr | Leu |
| Arg | Ile | Ile | Lys | Gln | Glu | Phe | Thr | Leu | Asn | Asp | Ala | Leu | Asn | Gln |
| Ser | Leu | Val | Arg | Asp | Thr | Ser | Asp | Gln | Tyr | Leu | Arg | Ala | Ala | Pro |
| Leu | Gln | Asn | Leu | Gly | Asp | Ala | Val | Lys | Phe | Asp | Met | Gly | Val | Tyr |
| Met | Thr | Ser | Glu | Asp | Ser | Ile | Leu | Pro | Val | Thr | Leu | Arg | Ile | Ser |
| Gln | Thr | Pro | Leu | Phe | Val | Ser | Ala | Gln | Asn | Glu | Asp | Glu | Pro | Val |
| Leu | Leu | Lys | Glu | Met | Pro | Glu | Thr | Pro | Arg | Ile | Ile | Thr | Asp | Ser |
| Glu | Ser | Asp | Ile | Leu | Phe | Phe | Trp | Glu | Thr | Gln | Gly | Asn | Lys | Asn |
| Tyr | Phe | Lys | Ser | Ala | Ala | Asn | Pro | Gln | Leu | Phe | Ile | Ala | Thr | Lys |
| Pro | Glu | His | Leu | Val | His | Met | Ala | Arg | Gly | Leu | Pro | Ser | Met | Thr |
| Asp | Phe | Gln | Ile | Ser | | | | | | | | | | |

[A-1]

TABLE 3-2

| | | | | | | | | | | | | |
|---|---|---|---|---|---|---|---|---|---|---|---|---|
| (5')TCA | GTT | CCT | TAC | ACC | TTC | CAG | AGA | AAT | ATG | AGA | TAC | AAA | TAC |
| TTG | AGA | ATC | ATC | AAA | CAA | GAG | TTT | ACC | CTG | AAT | GAT | GCT | CTC |
| AAT | CAA | AGC | CTA | GTT | CGT | GAC | ACC | TCA | GAT | CAG | TAC | CTC | AGG |
| GCA | GCT | CCA | CTA | CAA | AAT | CTG | GGC | GAT | GCA | GTG | AAA | TTT | GAC |
| ATG | GGG | GTC | TAC | ATG | ACA | TCA | GAG | GAT | TCT | ATA | CTT | CCT | GTA |
| ACG | TTA | AGA | ATC | TCA | CAA | ACT | CCA | CTG | TTT | GTG | AGT | GCC | CAG |
| AAT | GAA | GAT | GAA | CCT | GTG | CTG | CTA | AAG | GAA | ATG | CCT | GAG | ACA |
| CCC | AGG | ATC | ATC | ACA | GAC | AGC | GAG | AGT | GAC | ATC | CTC | TTC | TTC |
| TGG | GAA | ACG | CAA | GGC | AAT | AAG | AAC | TAC | TTC | AAG | TCA | GCA | GCC |
| AAC | CCA | CAG | CTG | TTT | ATT | GCC | ACA | AAG | CCA | GAA | CAT | CTG | GTG |
| CAC | ATG | GCA | AGG | GGG | TTA | CCT | TCG | ATG | ACT | GAT | TTT | CAG | ATC |
| TCA(3') | | | | | | | | | | | | | |

[B-1]

TABLE 4-1

| | | | | | | | | | | | | | |
|---|---|---|---|---|---|---|---|---|---|---|---|---|---|
| Met | Ala | Lys | Val | Pro | Asp | Leu | Phe | Glu | Asp | Leu | Lys | Asn | Cys | Phe |
| Ser | Glu | Asn | Glu | Glu | Tyr | Ser | Ser | Ala | Ile | Asp | His | Leu | Ser | Leu |
| Asn | Gln | Lys | Ser | Phe | Tyr | Asp | Ala | Ser | Tyr | Glu | Pro | Leu | His | Glu |
| Asp | Cys | Met | Asn | Lys | Val | Val | Ser | Leu | Ser | Thr | Ser | Glu | Thr | Ser |
| Val | Ser | Pro | Asn | Leu | Thr | Phe | Gln | Glu | Asn | Val | Val | Ala | Val | Thr |
| Ala | Ser | Gly | Lys | Ile | Leu | Lys | Lys | Arg | Arg | Leu | Ser | Leu | Asn | Gln |
| Pro | Ile | Thr | Asp | Val | Asp | Leu | Glu | Thr | Asn | Val | Ser | Asp | Pro | Glu |
| Glu | Gly | Ile | Ile | Lys | Pro | Arg | | | | | | | | |

[A-2]

TABLE 4-2

| | | | | | | | | | | | | |
|---|---|---|---|---|---|---|---|---|---|---|---|---|
| (5')ATG | GCC | AAA | GTC | CCT | GAT | CTG | TTT | GAA | GAC | CTA | AAG | AAC | TGT |
| TTC | AGT | GAA | AAT | GAG | GAA | TAC | AGC | TCT | GCC | ATT | GAC | CAT | CTT |
| TCT | CTG | AAT | CAG | AAA | TCC | TTC | TAT | GAT | GCA | AGC | TAT | GAA | CCA |
| CTT | CAT | GAA | GAC | TGC | ATG | AAT | AAA | GTT | GTG | TCT | CTG | AGT | ACC |
| TCT | GAA | ACC | TCT | GTG | TCA | CCC | AAC | CTC | ACC | TTC | CAG | GAG | AAT |
| GTG | GTG | GCA | GTA | ACA | GCC | AGT | GGG | AAG | ATT | CTG | AAG | AAA | AGA |
| CGC | TTG | AGT | TTA | AAC | CAG | CCC | ATC | ACG | GAT | GTT | GAC | CTG | GAG |
| ACC | AAT | GTC | AGT | GAT | CCA | GAA | GAA | GGA | ATC | ATC | AAG | CCC | AGA(3') |

[B-2]

TABLE 5

(human)

| 1 | | | | | | | | | 30 | | | | | | | | | | 60 |
|---|---|---|---|---|---|---|---|---|---|---|---|---|---|---|---|---|---|---|---|
| ATG | GCC | AAA | GTT | CCA | GAC | ATG | TTT | GAA | GAC | CTG | AAG | AAC | TGT | TAC | AGT | GAA | AAT | GAA | GAA |
| Met | Ala | Lys | Val | Pro | Asp | Met | Phe | Glu | Asp | Leu | Lys | Asn | Cys | Tyr | Ser | Glu | Asn | GLu | Glu |
| | | | | | | | | | 10 | | | | | | | | | | 20 |

| | | | | | | | | | 90 | | | | | | | | | | 120 |
|---|---|---|---|---|---|---|---|---|---|---|---|---|---|---|---|---|---|---|---|
| GAC | AGT | TCC | TCC | ATT | GAT | CAT | CTG | TCT | CTG | AAT | CAG | AAA | TCC | TTC | TAT | CAT | GTA | AGC | TAT |
| Asp | Ser | Ser | Ser | Ile | Asp | His | Leu | Ser | Leu | Asn | Gln | Lys | Ser | Phe | Tyr | His | Val | Ser | Tyr |
| | | | | | | | | | 30 | | | | | | | | | | 40 |

| | | | | | | | | 150 | | | | | | | | | | 180 |
|---|---|---|---|---|---|---|---|---|---|---|---|---|---|---|---|---|---|---|
| GGC | CCA | CTC | CAT | GAA | GGC | TGC | ATG | GAT | CAA | TCT | GTG | TCT | CTG | AGT | ATC | TCT | GAA | ACC | TCT |
| Gly | Pro | Leu | His | Glu | Gly | Cys | Met | Asp | Gln | Ser | Val | Ser | Leu | Ser | Ile | Ser | Glu | Thr | Ser |
| | | | | | | | | 50 | | | | | | | | | | 60 |

TABLE 5-continued (human)

|  |  |  |  |  |  |  |  |  | 210 |  |  |  |  |  |  |  |  |  | 240 |
|---|---|---|---|---|---|---|---|---|---|---|---|---|---|---|---|---|---|---|---|
| AAA | ACA | TCC | AAG | CTT | ACC | TTC | AAG | GAG | AGC | ATG | GTG | GTA | GTA | GCA | ACC | AAC | GGG | AAG | GTT |
| Lys | Thr | Ser | Lys | Leu | Thr | Phe | Lys | Glu | Ser | Met | Val | Val | Val | Ala | Thr | Asn | Gly | Lys | Val |
|  |  |  |  |  |  |  |  |  | 70 |  |  |  |  |  |  |  |  |  | 80 |

|  |  |  |  |  |  |  |  |  | 270 |  |  |  |  |  |  |  |  |  | 300 |
|---|---|---|---|---|---|---|---|---|---|---|---|---|---|---|---|---|---|---|---|
| CTG | AAG | AAG | AGA | CGG | TTG | AGT | TTA | AGC | CAA | TCC | ATC | ACT | GAT | GAT | GAC | CTG | GAG | GCC | ATC |
| Leu | Lys | Lys | Arg | Arg | Leu | Ser | Leu | Ser | Gln | Ser | Ile | Thr | Asp | Asp | Asp | Leu | GLu | Ala | Ile |
|  |  |  |  |  |  |  |  |  | 90 |  |  |  |  |  |  |  |  |  | 100 |

|  |  |  |  |  |  |  |  |  | 330 |  |  |  |  |  |  |  |  |  | 360 |
|---|---|---|---|---|---|---|---|---|---|---|---|---|---|---|---|---|---|---|---|
| GCC | AAT | GAC | TCA | GAG | GAA | GAA | ATC | ATC | AAG | CCT | AGG | ⌈TCA | TCA | CCT | TTT | AGC | TTC | CTG | AGC |
| Ala | Asn | Asp | Ser | Glu | Glu | Glu | Ile | Ile | Lys | Pro | Arg | Ser | Ser | Pro | Phe | Ser | Phe | Leu | Ser |
|  |  |  |  |  |  |  |  |  | 110 |  |  |  |  |  |  |  |  |  | 120 |

|  |  |  |  |  |  |  |  |  | 390 |  |  |  |  |  |  |  |  |  | 420 |
|---|---|---|---|---|---|---|---|---|---|---|---|---|---|---|---|---|---|---|---|
| AAT | GTG | AAA | TAC | AAC | TTT | ATG | AGG | ATC | ATC | AAA | TAC | GAA | TTC | ATC | CTG | AAT | GAC | GCC | CTC |
| Asn | Val | Lys | Tyr | Asn | Phe | Met | Arg | Ile | Ile | Lys | Tyr | Glu | Phe | Ile | Leu | Asn | Asp | Ala | Leu |
|  |  |  |  |  |  |  |  |  | 130 |  |  |  |  |  |  |  |  |  | 140 |

|  |  |  |  |  |  |  |  |  | 450 |  |  |  |  |  |  |  |  |  | 480 |
|---|---|---|---|---|---|---|---|---|---|---|---|---|---|---|---|---|---|---|---|
| AAT | CAA | AGT | ATA | ATT | CGA | GCC | AAT | GAT | CAG | TAC | CTC | ACG | GCT | GCT | GCA | TTA | CAT | AAT | CTG |
| Asn | Gln | Ser | Ile | Ile | Arg | Ala | Asn | Asp | Gln | Tyr | Leu | Thr | Ala | Ala | ala | Leu | His | Asn | Leu |
|  |  |  |  |  |  |  |  |  | 150 |  |  |  |  |  |  |  |  |  | 160 |

|  |  |  |  |  |  |  |  |  | 510 |  |  |  |  |  |  |  |  |  | 540 |
|---|---|---|---|---|---|---|---|---|---|---|---|---|---|---|---|---|---|---|---|
| GAT | GAA | GCA | GTG | AAA | TTT | GAC | ATG | GGT | GCT | TAT | AAG | TCA | TCA | AAG | GAT | GAT | GCT | AAA | ATT |
| Asp | Glu | Ala | Val | Lys | Phe | Asp | Met | Gly | Ala | Tyr | Lys | Ser | Ser | Lys | Asp | Asp | Ala | Lys | Ile |
|  |  |  |  |  |  |  |  |  | 170 |  |  |  |  |  |  |  |  |  | 180 |

|  |  |  |  |  |  |  |  |  | 570 |  |  |  |  |  |  |  |  |  | 600 |
|---|---|---|---|---|---|---|---|---|---|---|---|---|---|---|---|---|---|---|---|
| ACC | GTG | ATT | CTA | AGA | ATC | TCA | AAA | ACT | CAA | TTG | TAT | GTG | ACT | GCC | CAA | GAT | GAA | GAC | CAA |
| Thr | Val | Ile | Leu | Arg | Ile | Ser | Lys | Thr | Gln | Leu | Tyr | Val | Thr | Ala | Gln | Asp | Glu | Asp | Gln |
|  |  |  |  |  |  |  |  |  | 190 |  |  |  |  |  |  |  |  |  | 200 |

|  |  |  |  |  |  |  |  |  | 630 |  |  |  |  |  |  |  |  |  | 660 |
|---|---|---|---|---|---|---|---|---|---|---|---|---|---|---|---|---|---|---|---|
| CCA | GTG | CTG | CTG | AAG | GAG | ATG | CCT | GAG | ATA | CCC | AAA | ACC | ATC | ACA | GGT | AGT | GAG | ACC | AAC |
| Pro | Val | Leu | Leu | Lys | Glu | Met | Pro | Glu | Ile | Pro | Lys | Thr | Ile | Thr | Gly | Ser | Glu | Thr | Asn |
|  |  |  |  |  |  |  |  |  | 210 |  |  |  |  |  |  |  |  |  | 220 |

|  |  |  |  |  |  |  |  |  | 690 |  |  |  |  |  |  |  |  |  | 720 |
|---|---|---|---|---|---|---|---|---|---|---|---|---|---|---|---|---|---|---|---|
| CTC | CTC | TTC | TTC | TGG | GAA | ACT | CAC | GGC | ACT | AAG | AAC | TAT | TTC | ACA | TCA | GTT | GCC | CAT | CCA |
| Leu | Leu | Phe | Phe | Trp | Glu | Thr | His | Gly | Thr | Lys | Asn | Tyr | Phe | Thr | Ser | Val | Ala | His | Pro |
|  |  |  |  |  |  |  |  |  | 230 |  |  |  |  |  |  |  |  |  | 240 |

|  |  |  |  |  |  |  |  |  | 750 |  |  |  |  |  |  |  |  |  | 780 |
|---|---|---|---|---|---|---|---|---|---|---|---|---|---|---|---|---|---|---|---|
| AAC | TTG | TTT | ATT | GCC | ACA | AAG | CAA | GAC | TAC | TGG | GTG | TGC | TTG | GCA | GGG | GGG | CCA | CCC | TCT |
| Asn | Leu | Phe | Ile | Ala | Thr | Lys | Gln | Asp | Tyr | Trp | Val | Cys | Leu | Ala | Gly | Gly | Pro | Pro | Ser |
|  |  |  |  |  |  |  |  |  | 250 |  |  |  |  |  |  |  |  |  | 260 |

|  |  |  |  |  |  |  |  |  | 810 |  |  |  |  |  |  |  |  |  | 840 |
|---|---|---|---|---|---|---|---|---|---|---|---|---|---|---|---|---|---|---|---|
| ATC | ACT | GAC | TTT | CAG | ATA | CTG | GAA | AAC | CAG | GCG | ⌉TAG | GTC | TGG | AGT | CTC | ACT | TGT | CTC | ACT |
| Ile | Thr | Asp | Phe | Gln | Ile | Leu | Glu | Asn | Gln | Ala | *** |  |  |  |  |  |  |  |  |
|  |  |  |  |  |  |  |  |  | 270 |  |  |  |  |  |  |  |  |  |  |

[Note]:
1) *** means the stop codon.
2) The bracket means the region coding for mature IL-1.

TABLE 6
(human)

```
1
Met Ala Lys Val Pro Asp Met Phe Glu Asp Leu Lys Asn Cys Tyr Se    r Glu Asn Glu Glu
                              10                                                    20
ATG GCC AAA GTT CCA GAC ATG TTT GAA GAC CTG AAG AAC TGT TAC AG---(intron 2)---T GAA AAT GAA GAA Lys Ser Phe Tyr His Val Ser Tyr
Asp Ser Ser Ile Asp His Leu Ser Leu Asn Gln                                                     40
                    30
GAC AGT TCC ATT GAT CAT CTG TCT CTG AAT CAG---(intron 3)---- AAA TCC TTC TAT CAT GTA AGC TAT Gly Pro Leu His Glu Gly Cys Met Asp Gln Ser Val Ala Thr Asn Gly Lys Val Leu Lys Arg Arg Leu Ser Leu
                              50                                60
GGC CCA CTC CAT GAA GGC TGC ATG GAT CAA TCT GTG GCA ACC AAC GGG AAG GTT CTG AAG AGA CGG TTG AGT TTA Leu Thr Phe Lys Glu Ser Met             Val Val Ala Thr Asn Gly Lys Val Leu Lys Lys Arg Arg        lu Ile
        70                                              80
CTT ACC TTC AAG GAG AGC ATG                                                                     AA ATC Ser Gln Ser Ile Thr Asp Asp Leu Glu Ala Ile Ala Asn Asp Ser Glu Glu G
        90                                      100
AGC CAA TCC ATC ACT GAT GAT CTG GAG GCC ATC GCC AAT GAC TCA GAG GAA G---(intron 4)----

Ile Lys Pro Arg Ser Ser Pro Phe Leu Ser Asn Gln Ser Ile Ile Arg Ala Asn Phe Met Arg Ile Lys Tyr
                              110                             120                      130
ATC AAG CCT AGG TCA TCA CCT TTT CTC AGC AAT CAA AGT ATA ATT CGA GCC AAT TTC ATG AGG ATC AAA TAC

Glu Phe Ile Leu Asn Asp Ala Leu Asn Gln Leu           al Lys Phe Asp Met Gly Ala Tyr Lys Ser Ser Lys Asp Ala
                              140                                              150                170
GAA TTC ATC CTG AAT GAC GCC CTC AAT CAA CTA V---(intron 5)----TG AAA TTT GAC ATG GGT GCT TAT AAG TCA TCA AAG GAT GCA Leu His Asn Leu Asp Glu Ala
        160
TTA CAT AAT CTG GAT GAA GCA ---to be continued---
```

Table 6 (human) (continued)

```
                    180                                       190                                         200
Asp Ala Lys Ile Thr Val Ile Leu Arg Ile Ser Lys Thr Gln Leu Tyr Val Thr Ala Gln Asp Glu Asp Gln
GAT GCT AAA ATT ACC GTG ATT CTA AGA ATC TCA AAA ACT CAA TTG TAT GTG ACT GCC CAA GAT GAA GAC CAA 210                                                             220
            Glu Met Pro Glu Ile Pro Lys Thr Tyr Phe Thr Ile Thr Gly Ser Glu Thr Asn
Pro Val Leu Lys
CCA GTG CTG AAG----(intron 6)---- GAG ATG CCT GAG ATA CCC AAA ACC TAT TTC ACA ATC ACA GGT AGT GAG ACC AAC 230                                                      240
Leu Phe Phe Trp Glu Thr His Gly Thr Lys Asn Tyr Phe Thr Ser Val Ala His Pro Asn Leu Phe Ile
CTC TTC TTC TGG GAA ACT CAC GGC ACT AAG AAC TAT TTC ACA TCA GTT GCC CAT CCA AAC TTG TTT ATT 250                                       260
Ala Thr Lys Gln Asp Tyr Trp Val Cys Leu Ala Gly Gly Pro Pro Ser Ile Thr Asp Phe Gln Ile Leu Glu
GCC ACA AAG CAA GAC TAC TGG GTG TGC TTG GCA GGG GGA CCA CCC TCT ATC ACT GAC TTT CAG ATA CTG GAA 271
Asn Gln Ala ***
AAC CAG GCG TAG
```

[Note]:
\*\*\*means the stop condon.

TABLE 7

(rabbit)

| | | | | | | | | | | | | | | | | | | | |
|---|---|---|---|---|---|---|---|---|---|---|---|---|---|---|---|---|---|---|---|
| 1 | | | | | | | | | 30 | | | | | | | | | | 60 |
| ATG | GCC | AAA | GTC | CCT | GAT | CTG | TTT | GAA | GAC | CTA | AAG | AAC | TGT | TTC | AGT | GAA | AAT | GAA | GAA |
| Met | Ala | Lys | Val | Pro | Asp | Met | Phe | Glu | Asp | Leu | Lys | Asn | Cys | Phe | Ser | Glu | Asn | GLu | Glu |
| | | | | | | | | | 10 | | | | | | | | | | 20 |
| | | | | | | | | | 90 | | | | | | | | | | 120 |
| TAC | AGC | TCT | GCC | ATT | GAC | CAT | CTT | TCT | CTG | AAT | CAG | AAA | TCC | TTC | TAT | GAT | GCA | AGC | TAT |
| Tyr | Ser | Ser | Ala | Ile | Asp | His | Leu | Ser | Leu | Asn | Gln | Lys | Ser | Phe | Tyr | Asp | Ala | Ser | Tyr |
| | | | | | | | | | 30 | | | | | | | | | | 40 |
| | | | | | | | | | 150 | | | | | | | | | | 180 |
| GAA | CCA | CTT | CAT | GAA | GAC | TGC | ATG | AAT | AAA | GTT | GTG | TCT | CTG | AGT | ACC | TCT | GAA | ACC | TCT |
| Glu | Pro | Leu | His | Glu | Asp | Cys | Met | Asn | Lys | Val | Val | Ser | Leu | Ser | Thr | Ser | Glu | Thr | Ser |
| | | | | | | | | | 50 | | | | | | | | | | 60 |
| | | | | | | | | | 210 | | | | | | | | | | 240 |
| GTG | TCA | CCC | AAC | CTC | ACC | TTC | CAG | GAG | AAT | GTG | GTG | GCA | GTA | ACA | GCC | AGT | GGG | AAG | ATT |
| Val | Ser | Pro | Asn | Leu | Thr | Phe | Gln | Glu | Asn | Val | Val | Ala | Val | Thr | Ala | Ser | Gly | Lys | Ile |
| | | | | | | | | | 70 | | | | | | | | | | 80 |
| | | | | | | | | | 270 | | | | | | | | | | 300 |
| CTG | AAG | AAG | AGA | CGC | TTG | AGT | TTA | AAC | CAG | CCC | ATC | ACT | GAT | GTT | GAC | CTG | GAG | ACC | AAT |
| Leu | Lys | Lys | Arg | Arg | Leu | Ser | Leu | Ser | Gln | Pro | Ile | Thr | Asp | Val | Asp | Leu | GLu | Thr | Asn |
| | | | | | | | | | 90 | | | | | | | | | | 100 |
| | | | | | | | | | 330 | | | | | | | | | | 360 |
| GTC | AGT | GAT | CCA | GAA | GAA | GAA | ATC | ATC | AAG | CCC | AGA | ⌈TCA | GTT | CCT | TAC | ACC | TTC | CAG | AGA |
| Val | Ser | Asp | Pro | Glu | Glu | Gly | Ile | Ile | Lys | Pro | Arg | ⌊Ser | Val | Pro | Tyr | Thr | Phe | Gln | Arg |
| | | | | | | | | | 110 | | | | | | | | | | 120 |
| | | | | | | | | | 390 | | | | | | | | | | 420 |
| AAT | ATG | AGA | TAC | AAA | TAC | TTG | AGA | ATC | ATC | AAA | CAA | GAG | TTT | ACC | CTG | AAT | GAT | GCT | CTC |
| Asn | Met | Arg | Tyr | Lys | Tyr | Leu | Arg | Ile | Ile | Lys | Gln | Glu | Phe | Thr | Leu | Asn | Asp | Ala | Leu |
| | | | | | | | | | 130 | | | | | | | | | | 140 |
| | | | | | | | | | 450 | | | | | | | | | | 480 |
| AAT | CAA | AGC | CTA | GTT | CGT | GAC | ACC | TCA | GAT | CAG | TAC | CTC | AGG | GCA | GCT | CCA | CTA | CAA | AAT |
| Asn | Gln | Ser | Leu | Val | Arg | Asp | Thr | Ser | Asp | Gln | Tyr | Leu | Arg | Ala | Ala | Pro | Leu | Gln | Asn |
| | | | | | | | | | 150 | | | | | | | | | | 160 |
| | | | | | | | | | 510 | | | | | | | | | | 540 |
| CTG | GGC | GAT | GCA | GTG | AAA | TTT | GAC | ATG | GGG | GTC | TAC | ATG | ACA | TCA | GAG | GAT | TCT | ATA | CTT |
| Leu | Gly | Asp | Ala | Val | Lys | Phe | Asp | Met | Gly | Val | Tyr | Met | Thr | Ser | Glu | Asp | Ser | Ile | Leu |
| | | | | | | | | | 170 | | | | | | | | | | 180 |
| | | | | | | | | | 570 | | | | | | | | | | 600 |
| CCT | GTA | ACT | TTA | AGA | ATC | TCA | CAA | ACT | CCA | CTG | TTT | GTG | AGT | GCC | CAG | AAT | GAA | GAT | GAA |
| Pro | Val | Thr | Leu | Arg | Ile | Ser | Gln | Thr | Pro | Leu | Phe | Val | Ser | Ala | Gln | Asn | Glu | Asp | Glu |
| | | | | | | | | | 190 | | | | | | | | | | 200 |
| | | | | | | | | | 630 | | | | | | | | | | 660 |
| CCT | GTG | CTG | CTA | AAG | GAA | ATG | CCT | GAG | ACA | CCC | AGG | ATC | ATC | ACA | GAC | AGC | GAG | AGT | GAC |
| Pro | Val | Leu | Leu | Lys | Glu | Met | Pro | Glu | Thr | Pro | Arg | Ile | Ile | Thr | Asp | Ser | Glu | Ser | Asp |
| | | | | | | | | | 210 | | | | | | | | | | 220 |
| | | | | | | | | | 690 | | | | | | | | | | 720 |
| ATC | CTC | TTC | TTC | TGG | GAA | ACT | CAA | GGC | AAT | AAG | AAC | TAC | TTC | AAG | TCA | GCA | GCC | AAC | CCA |
| Ile | Leu | Phe | Phe | Trp | Glu | Thr | Gln | Gly | Asn | Lys | Asn | Tyr | Phe | Lys | Ser | Ala | Ala | Asn | Pro |
| | | | | | | | | | 230 | | | | | | | | | | 240 |
| | | | | | | | | | 750 | | | | | | | | | | 780 |
| CAG | CTG | TTT | ATT | GCC | ACA | AAG | CCA | GAA | CAT | CTG | GTG | CAC | ATG | GCA | AGG | GGG | TTA | CCT | TCG |
| Gln | Leu | Phe | Ile | Ala | Thr | Lys | Pro | Glu | His | Leu | Val | His | Met | Ala | Arg | Gly | Leu | Pro | Ser |
| | | | | | | | | | 250 | | | | | | | | | | 260 |
| | | | | | 801 | | | | | | | | | | | | | | |
| ATG | ACT | GAT | TTT | CAG | ATC | TCA⌉ | TAA | | | | | | | | | | | | |
| Met | Thr | Asp | Phe | Gln | Ile | Ser⌋ | *** | | | | | | | | | | | | |
| | | | | | | 267 | | | | | | | | | | | | | |

[Note]:
1) ***means the stop codon.
2) The bracket means the region coding for mature IL-1.

TABLE 8-1

| ATC GCC AAA GTC CCT GAT CTG TTT GAA GAC CTA AAG AAC TGT AGT GAA AAT GAG GAA TCT GCC |
| ATG GCC AAA GTT CCA GAC GAC CTG TTT GAA GAC CTG AAC AAC TGT AGT AGT GAA AAT GAA TCC ATG |

| ATT GTC CAT CTT TCT CTG AAT CAG AAA TCC TTT TAT GAT GCA AGC TAT GAA AAT TGA CTG ATG |
| ATT GAT CAT CTG TCT CTG AAT CAG AGT AGC TTC TAT GAT GAT CCA TAT GGC TGC TGC GAA GAC |

| AAT GGT GTG TCT CTG AGT ACC TCT GAA ACC TTA CTG GTG ACC TTA ACC TTA CAG AAT GTG GTG |
| CAA TCT GTG TCT CTG AGT AGT ATC TCT GAA ACC TCT AAA GTT TCA CTC CTT AGT ATG GAC |

| ACA GTT GCC AAT ATT CTG AAG AAA AGA CGC CCC ATC ACT ACT CAA AAA TTT GAC |
| GCA GTT GCT ACC ATC CTG AAG AAG AGA CGG ATC ATC ACT ACT GGC GCA GTG ATT TTT GAC |

| CTG GAG ACC AAT GCT GAT GAT CCA CCT GAG TTA AGA ATC TCA GGC GAT CTG AAT GAT CTA CTG |
| CTG GAG GAG GTA AAC GCC ATC CTG AAG GAA GAA TCA AGA GAC GAG TTC CTG ATG CTG AGC |

| AAT ATG TAC AAA TAC TTG AGA CAG GAG TTT ACT CCA CAA GGT GCT AAT ATG GAC |
| AAT GTG TCA AAC AAG AGG ATG TAC AAC AAA TAC GAA TTG AGG CTG CTA CTC |

| CTT CCT AAT ATC CAA TAC CTC AGG GCA GCC TTA GAT TCA GAT CAG TAC CTC AGG GCA GCC TTA |
| AAT GGC ATT CTG CAT CTG CTA CAG AAT CAG ATT CAT CAG AGC CAG AAT GCC ATG |

| TTT GGG ATC GAA GAT CCT GAG TTA AGA ATC TCA GAT CAG TAC CTC AGG GCA GCC TTA GAT |
| ATG GCT GGG TCA GAA GAC CCA CCT GAG TTA AGA ATC TCA GAT CAG TAC CTC AGG GCA GCC TTA |

| ATG GGG AGT ACC AAT TAC TGG AGA AGC TCA TTC AAG AAC TAC TCA GCC AGC |
| ATG GGT AAC AAT TAC TTC AGA AGC TCA TTC AAG AAC TAC TCA GCC AGT |

| GAC AGC AGT GAG GAA CAA ACA GTT TCA GCC AGT |
| GGT AGT ACC GAG GAG CAC CAC GTT TCA GCC AGT |

TABLE 8-1-continued

| CCA | CTG | TTT | ATT | GCC | ACA | AAG | CCA | GAA | CAT | CTG | GTC | CAG | ATG | GTG | AGG | GGG | TTA | CCT | TGG | ATG | ACT | GAT |
| CCA | TTG | TTT | ATT | GCC | ACA | AAG | CAA | GAC | TAC | TGG | GTC | TGC | TTG | GCA | GGG | GGG | CCA | CCC | TCT | ATC | ACT | GAC |

| | | | | | | | *** | | |
| TTT | CAG | ATC | TCA | TAA | AAC | CAG | CCT | TAG | | |
| TTT | CAG | ATA | CTG | GAA | AAC | CAG | GGG | TAG | | |
| | | | | | | | *** | | |

[Note]:
1) Upper sequence is the nucleotide sequence of a DNA encoding rabbit IL-1 precursor.
2) Lower sequence is the nucleotide sequence of a DNA encoding human IL-1 precursor.
3) - - - means deletion.
4) *** means the stop codon.
5) The regions surrounded by  are homologous regions.

TABLE 8-2

| | | | | | | | | | | | | | | | | | | | | | |
|---|---|---|---|---|---|---|---|---|---|---|---|---|---|---|---|---|---|---|---|---|---|
| Met Ala Lys Val Pro Asp | | | | | | Leu Met | Phe Glu Asp Leu Lys Asn Cys | | | | | | | Phe Tyr | Ser Glu Asn Glu Glu | | | | | Tyr Asp | Ser Ser Ser Ser | |
| Ala Ser | Ile Asp His Leu Ser Leu Asn Gln Lys Ser Phe Tyr | | | | | | | | | | | Asp Ala His Val | Ser Tyr Ser Tyr | | Glu Gly | Pro Leu His Glu | | | | Asp Gly | |
| Cys Met Cys Met | | Asn Lys Val Asp Gln Ser | | | Val Ser Leu Ser Val Ser Leu Ser | | | Thr Ile | Ser Glu Thr Ser Ser Glu Thr Ser | | | | Val Ser Pro Asn Lys Thr Ser Lys | | | | Leu Thr Phe Leu Thr Phe | | | Gln Lys | Glu Glu | |
| Asn Val Ser Met | Val Val | Ala Val | Val Val | Thr Ala Ser Ala Thr Asn | | | Gly Lys Gly Lys | | Ile Val | Leu Lys Lys Arg Arg Leu Ser Leu Leu Lys Lys Arg Arg Leu Ser Leu | | | | | | | Asn Ser | Gln Gln | Pro Ser | Ile Ile | |
| Thr Asp Thr Asp | | Val Asp | Asp Leu Glu Asp Leu Glu | | | Thr Asn Val Ser Ala Ile Ala Asn | | | | Asp Asp | Pro Ser | Glu Glu Glu Glu | | Gly Glu | Ile Ile Lys Pro Arg Ser Ile Ile Lys Pro Arg Ser | | | | | Val Ser | Pro Pro |
| Tyr Thr Phe Ser | | Phe Phe | Gln Arg Leu Ser | | Asn Asn | Met Arg Val Lys | | Tyr Tyr | Lys Tyr Leu Asn Phe Met | | | Arg Ile Ile Lys Arg Ile Ile Lys | | | Gln Tyr | Glu Phe Glu Phe | | Thr Ile | Leu Asn Asp Leu Asn Asp | | |
| Ala Leu Asn Gln Ser Ala Leu Asn Gln Ser | | | | Leu Val Ile Ile | | Arg Arg | Asp Thr Ser Ala Asn --- | | | Asp Gln Tyr Leu Asp Gln Tyr Leu | | | Arg Thr | Ala Ala Ala Ala | | Pro Ala | Leu Leu | Gln His | Asn Leu Asn Leu | | |
| Gly Asp Asp Glu | Ala Val Lys Phe Asp Met Gly Ala Val Lys Phe Asp Met Gly | | | | | | Val Ala | Tyr Tyr | Met Thr Lys Ser | | Ser Ser | --- Lys Asp | Glu Asp | Asp | Ser Ile Leu Pro Ala Lys Ile Thr | | | | Val Val | Thr Ile | |
| Leu Arg Ile Ser Leu Arg Ile Ser | | | | Gln Lys | Thr Thr | Pro Gln | Leu Leu | Phe Tyr | Val Val | Ser Thr | Ala Gln Ala Gln | | Asn Asp | Glu Asp Glu Asp | | Glu Gln | Pro Val Leu Leu Lys Glu Pro Val Leu Leu Lys Glu | | | | |
| Met Pro Glu Met Pro Glu | | | Thr Ile | Pro Pro | Arg Ile Lys Thr | | Ile Thr Ile Thr | | Asp Gly | Ser Glu Ser Glu | | Ser Asp Ile Thr Asn Leu | | | Leu Phe Phe Trp Glu Thr Leu Phe Phe Trp Glu Thr | | | | | Gln His | Gly Gly |
| Asn Thr | Lys Asn Tyr Phe Lys Asn Tyr Phe | | | Lys Thr | Ser Ser | Ala Val | Ala Ala | Asn His | Pro Pro | Gln Asn | Leu Phe Ile Ala Thr Lys Leu Phe Ile Ala Thr Lys | | | | | Pro Glu His Leu Gln Asp Tyr Trp | | | | | Val Val |
| His Met Cys Leu | | Ala Ala | Arg Gly | Gly Gly | Leu Pro | Pro Ser Pro Ser | | Met Ile | Thr Asp Phe Gln Ile Thr Asp Phe Gln Ile | | | | Ser Leu | --- Glu | --- Asn | --- Gln | --- Ala | | | | |

[Note]:
1) Upper sequence is polypeptide of rabbit IL-1 precursor.
2) Lower sequence is polypeptide of human IL-1 precursor.
3) --- means deletion.
4) the regions surrounded by ☐ are homologous regions.

What is claimed is:

1. A method of treating sarcoma in an animal which comprises administering an isolated mature human interleukin 1α polypeptide in an amount effective to treat said sarcoma wherein said polypeptide has an amino acid sequence selected from the group consisting of amino acids 113 to 271, 128 to 271, 113 to 267 and 128 to 267 of FIG. 11.

* * * * *

UNITED STATES PATENT AND TRADEMARK OFFICE
CERTIFICATE OF CORRECTION

PATENT NO. : 5,376,639
DATED : December 27, 1994
INVENTOR(S) : Masaaki Yamada, et al.

Page 1 of 2

It is certified that error appears in the above-indentified patent and that said Letters Patent is hereby corrected as shown below:

Column 14, line 18: "16,000" should read --17,100--.

Column 22, line 46: "of clones" should read --of six clones--

Column 24, line 40: "$H_2$," should read --$H_2O$,--

Column 27, line 35: after "B-16" delete --.--

Column 36, lines 42, 45 & 47, Table 1-2: "ACG." should read --ACT--

Column 38, line 51, Table 4-2: "ACG" should read --ACT--

Column 45, line 5, Table 7: "Met" should read --Leu-- (under #30, 2nd line).

Column 45, line 20, Table 7: "AAG" should read --AAA-- (under #270, 2nd occur.).

Column 45, line 21, Table 7: "Ser" should read --Asn--(under #270, 2nd occur.).

UNITED STATES PATENT AND TRADEMARK OFFICE
CERTIFICATE OF CORRECTION

PATENT NO. : 5,376,639
DATED : December 27, 1994
INVENTOR(S) : Masaaki Yamada, et al.

It is certified that error appears in the above-indentified patent and that said Letters Patent is hereby corrected as shown below:

Column 48, line 65, Table 8-1: "CTG" should read --GTG--

Column 51, line 54, Table 8-1: "the" should read --The--

Signed and Sealed this

Twenty-sixth Day of March, 1996

Attest:

BRUCE LEHMAN

*Attesting Officer*      *Commissioner of Patents and Trademarks*